United States Patent [19]
Linz et al.

[11] Patent Number: 5,607,944
[45] Date of Patent: Mar. 4, 1997

[54] BICYCLIC HETEROCYCLIC COMPOUNDS, PHARMACEUTICAL PREPARATIONS CONTAINING THESE COMPOUNDS AND PROCESSES FOR THEIR PREPARATIONS

[75] Inventors: Günter Linz; Frank Himmelsbach, both of Mittelbiberach; Helmut Pieper; Volkhard Austel, both of Biberach; Thomas Müller, Edewecht; Johannes Weisenberger, Biberach; Brian Guth, Warthausen, all of Germany

[73] Assignee: Karl Thomae GmbH, Biberach an Riss, Germany

[21] Appl. No.: 509,248

[22] Filed: Jul. 31, 1995

Related U.S. Application Data

[63] Continuation of Ser. No. 278,435, Jul. 21, 1994, abandoned.

[30] Foreign Application Priority Data

Jul. 22, 1993 [DE]  Germany .................. 43 245 803.3

[51] Int. Cl.$^6$ ............... A61K 31/435; C07D 471/04
[52] U.S. Cl. ............... 514/301; 514/300; 514/302; 514/303; 540/481; 540/593; 546/23; 546/114; 546/115; 546/118
[58] Field of Search ................ 514/215, 301, 514/300, 302, 303; 540/481, 593; 546/23, 114, 115, 118

[56] References Cited

U.S. PATENT DOCUMENTS 3,985,891  10/1976  Kutter et al. .................. 546/118

FOREIGN PATENT DOCUMENTS

| 0079083 | 5/1983  | European Pat. Off. . |  |
| 0296455 | 12/1988 | European Pat. Off. . |  |
| 0351856 | 1/1990  | European Pat. Off. . |  |
| 0397614 | 11/1990 | European Pat. Off. ........ | 546/118 |
| 0407217 | 1/1991  | European Pat. Off. . |  |
| 0546449 | 6/1993  | European Pat. Off. ........ | 546/118 |
| 0560330 | 9/1993  | European Pat. Off. . |  |
| 0567967 | 11/1993 | European Pat. Off. . |  |
| 0581166 | 2/1994  | European Pat. Off. . |  |
| 3621112 | 1/1988  | Germany ................ | 546/118 |
| 3722992 | 1/1989  | Germany . |  |
| 1019084 | 1/1989  | Japan . |  |
| 2093030 | 8/1982  | United Kingdom ............ | 540/593 |
| 2264115 | 8/1993  | United Kingdom . |  |

Primary Examiner—Yogendra N. Gupta
Attorney, Agent, or Firm—Robert P. Raymond; Alan R. Stempel; Mary-Ellen M. Devlin

[57] ABSTRACT

The invention relates to bicyclic heterocyclic compounds of general formula

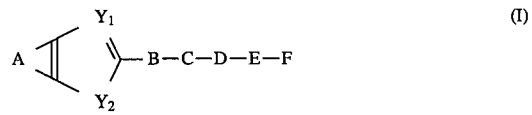

wherein A to F, $Y_1$ and $Y_2$ are defined as in claim 1, the tautomers thereof, the stereoisomers thereof including their mixtures, and salts thereof, particularly the physiologically acceptable salts thereof with organic or inorganic acids or bases, which have valuable pharmacological properties, preferably aggregation-inhibiting effects, pharmaceutical compositions containing the compounds and processes for preparing them as well as new intermediate products of general formula Ia.

7 Claims, No Drawings

BICYCLIC HETEROCYCLIC COMPOUNDS, PHARMACEUTICAL PREPARATIONS CONTAINING THESE COMPOUNDS AND PROCESSES FOR THEIR PREPARATIONS

This is a Continuation of application Ser. No. 08/278,435, filed Jul. 21, 1994, now abandoned.

The invention relates to bicyclic heterocyclic compounds of general formula

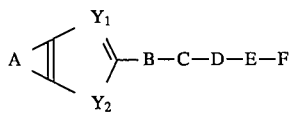

the tautomers thereof, the stereoisomers thereof including mixtures thereof and the salts thereof, particularly the physiologically acceptable salts with inorganic or organic acids or bases, which have valuable pharmacological properties, preferably anti-aggregatory effects, pharmaceutical compositions containing these compounds and the use thereof, as well as processes for preparing them.

In general formula I above $Y_1$ denotes a nitrogen atom or a carbon atom substituted by a group $R_1$, wherein
  $R_1$ denotes a hydrogen atom or an alkyl group;

$Y_2$ denotes a nitrogen atom substituted by a group $R_1$, wherein $R_1$ is as hereinbefore defined, or $Y_2$ denotes an oxygen or sulphur atom;

A denotes an $-N=CH-NR_2-(CH_2)_m-$, $-(CH_2)_m-NR_2-CH=N-$, $-CH=CH-N=CH-$, $-CH=N-CH=CH-$ or $-(CH_2)_n-NR_2-(CH_2)_p-$ bridge, which may be substituted by one or two alkyl groups in the carbon moiety, wherein
  m denotes the number 1 or 2,
  n and p, which may be identical or different, each represent the number 1, 2 or 3 and
  $R_2$ denotes a hydrogen atom, an alkoxycarbonyl group having a total of 2 to 7 carbon atoms, an alkyl, phenylalkyl, allyloxycarbonyl, phenylalkoxycarbonyl, trifluoromethylcarbonyl, $R_1CO-$ or $R_3CO-O-CHR_1-OCO-$ group wherein $R_1$ is as hereinbefore defined and
  $R_3$ denotes a $C_{1-5}$-alkyl group, a $C_{5-7}$-cycloalkyl group, a phenylalkyl group or a phenyl group;

B denotes a phenylene group optionally mono- or disubstituted by a fluorine, chlorine or bromine atom or by a cyano, trifluoromethyl, alkyl, hydroxy, alkoxy, alkylsulphenyl, alkylsulphinyl or alkylsulphonyl group, wherein the substituents may be identical or different and wherein additionally 1 or 2 methine groups may each be replaced by an N-atom, or B denotes a 1,4-cyclohexylene group wherein a >CH— unit in the 1- or 4-position may be replaced by a nitrogen atom or the >CH— units in the 1- and 4-position may each be replaced by a nitrogen atom, or B denotes a 1,4-cyclohexylene group wherein the methylene group in the 2-position or the methylene groups in the 2- and 5-positions are each replaced by an $-NR_4$ group, whilst in a ring thus obtained which contains one or two nitrogen atoms or one or two $-NR_4$ groups, one or two methylene groups adjacent to a nitrogen atom may be replaced by a carbonyl group, but only one carbonyl group may be adjacent to each ring nitrogen atom, or B denotes a 3,4-dehydro-1,4-piperidinylene or 1,3-piperidinylene group, wherein $R_4$ denotes a hydrogen atom or an alkyl or phenylalkyl group;

C denotes a $-CH_2-$, $-CH_2CH_2-$, $-CO-$, $-CH_2-SO_2-$ or $-SO_2-CH_2-$ group, or C denotes a $-CH_2-CO-$ or $-NR_4-CO-$ group, wherein the carbonyl group in each case is bound to group D and $R_4$ is as hereinbefore defined, or C denotes a $-CH_2-NR_4-$, $-NR_4-CH_2-$, $-O-CH_2-$, $-CH_2O-$, $-S-CH_2-$, $-CH_2-S$, $-SO-CH_2-$ or $-CH_2-SO-$, wherein the sulphinyl group, or a nitrogen, oxygen or sulphur atom may not be bound directly or via a single carbon atom to a nitrogen atom of groups B or D, and $R_4$ is as hereinbefore defined;

D denotes a 1,4-cyclohexylene or 1,4-cyclohex-3-enylene group wherein one or both >CH— units bound to groups C, E or F may be replaced by a nitrogen atom and the >CH— unit bound to group E or F may also be replaced by a >C=CH— group, or D denotes an $-NR_5-X$ group, wherein
  X denotes a straight-chain or branched $C_{1-5}$-alkylene group or a 1,4-cyclohexylene group and
  $R_5$ denotes a hydrogen atom, a phenylalkyl group having 1 to 4 carbon atoms in the alkyl moiety, or a $C_{1-6}$-alkyl group which may be substituted in the 1-, 2- or 3-position by a morpholinocarbonyl, pyrrolidinocarbonyl, piperidinocarbonyl or hexamethyleneiminocarbonyl group or by an $(R_6NR_7)-CO-$ group, wherein
  $R_6$ denotes a hydrogen atom, a $C_{1-5}$-alkyl group, a $C_{5-7}$-cycloalkyl group, or a phenyl or phenylalkyl group and
  $R_7$ denotes a hydrogen atom, a $C_{1-4}$-alkyl group, a $C_{5-7}$-cycloalkyl group or a phenyl group;

E denotes an alkylene group or, if D is not directly bound to group F via a nitrogen atom, E may also denote a bond; and F denotes a carbonyl group substituted by an $R_8O-$ group, wherein
  $R_8$ denotes a hydrogen atom, a $C_{1-6}$-alkyl group which may be substituted in the 1-, 2- or 3-position by a morpholinocarbonyl, pyrrolidinocarbonyl, piperidinocarbonyl, hexamethyleneiminocarbonyl or $(R_6NR_7)-CO-$ group, wherein $R_6$ and $R_7$ are as hereinbefore defined, or in the 2- or 3-position by a morpholino or pyrrolidinon-1-yl group, or $R_8$ denotes a phenylalkyl or pyridylalkyl group, or $R_8$ denotes a $C_{4-8}$-cycloalkyl group or a cycloalkylalkyl group having 3 to 8 carbon atoms in the cycloalkyl moiety, wherein the cycloalkyl moiety may be substituted by a $C_{1-4}$-alkyl group or by a $C_{1-4}$-alkyl group and by 1 to 3 methyl groups, or $R_8$ denotes a bicycloalkyl or bicycloalkylalkyl group in which the bicycloalkyl moiety in each case contains 6 to 10 carbon atoms and additionally may be substituted by 1 to 3 methyl groups, or $R_8$ denotes an indanyl or cinnamyl group, or F denotes a phosphono, O-alkylphosphono or $R_9CO-O-CHR_6-O-CO-$ group, wherein
  $R_6$ is as hereinbefore defined and
  $R_9$ denotes a $C_{1-5}$-alkyl group, a cycloalkyl or cycloalkyloxy group each having 5 to 7 carbon atoms in the cycloalkyl moiety, a $C_{1-4}$-alkoxy group or a phenyl, phenylalkyl or phenylalkoxy group;

whilst unless otherwise specified the above-mentioned alkyl, alkylene or alkoxy moieties may each contain 1 to 3 carbon atoms.

The present invention further relates to the new intermediate products of general formula:

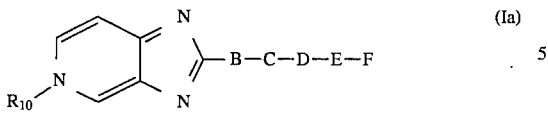

wherein

B to F are as hereinbefore defined and $R_{10}$ denotes an alkyl or phenylalkyl group each having 1 to 3 carbon atoms in the alkyl moiety, and the salts thereof.

Preferred compounds of general formula I above are those wherein $Y_1$ denotes a nitrogen atom or a carbon atom substituted by a group $R_1$, wherein
$R_1$ denotes a hydrogen atom or alkyl group;

$Y_2$ denotes a nitrogen atom substituted by a group $R_1$, wherein $R_1$ is as hereinbefore defined, or $Y_2$ denotes an oxygen or sulphur atom;

A denotes a —CH=CH—N=CH—, —CH=N—CH=CH— or —$(CH_2)_n$—$NR_2$—$(CH_2)_p$— bridge wherein
n and p, which may be identical or different, each represent the number 1, 2 or 3 and
$R_2$ denotes a hydrogen atom, an alkoxycarbonyl group having a total of 2 to 6 carbon atoms, or an alkyl, allyloxycarbonyl or trifluoromethylcarbonyl group;

B denotes a phenylene group optionally mono- or disubstituted by a fluorine, chlorine or bromine atom or by an alkyl, trifluoromethyl or alkoxy group, wherein the substituents may be identical or different and wherein, additionally, 1 or 2 methine groups may each be replaced by an N atom, or B denotes a 1,4-cyclohexylene group wherein a >CH— unit in the 1- or 4-position may be replaced by a nitrogen atom or the >CH— units in the 1- and 4-positions may each be replaced by a nitrogen atom, or B denotes a 3,4-dehydro-1,4-piperidinylene or 1,3-piperidinylene group;

C denotes a —$CH_2$—, —$CH_2CH_2$—, —CO—, —$CH_2$—$SO_2$— or —$SO_2$—$CH_2$— group, a —$CH_2CO$— or —$NR_4$—CO—group, wherein the carbonyl group in each case is bound to group D and $R_4$ denotes a hydrogen atom or an alkyl group, or C denotes a —$CH_2$—$NR_4$—, —$NR_4$—$CH_2$—, —O—$CH_2$—, —$CH_2$—O—, —S—$CH_2$—, —$CH_2$—S—, —SO—$CH_2$— or —$CH_2$—SO— group, whilst the sulphinyl group or a nitrogen, oxygen or sulphur atom may not be bound directly or via a carbon atom to a nitrogen atom of group B or D and $R_4$ is as hereinbefore defined;

D denotes a 1,4-cyclohexylene or 1,4-cyclohex-3-enylene group in which the >CH— unit in the 1-position which is bound to group C, or the >CH— unit in the 4-position which is bound to group E or F, or both >CH— units may be replaced by a nitrogen atom, whilst the >CH— unit in the 4-position may also be replaced by a >C=CH— group, or D denotes an —$NR_5$—X group wherein
X denotes a straight-chain or branched $C_{1-5}$-alkylene group or a 1,4-cyclohexylene group and
$R_5$ denotes a hydrogen atom, or an alkyl or phenylalkyl group;

E denotes an alkylene group or, if D is not directly linked to group F via an N atom, E may also denote a bond; and F denotes a carbonyl group substituted by an $R_8O$ group, wherein
$R_8$ denotes a hydrogen atom, a $C_{1-6}$-alkyl group which may be substituted in the 1-, 2- or 3-position by a phenyl or pyridyl group, or in the 2- or 3-position by a morpholino group, or $R_8$ denotes a $C_{4-8}$-cycloalkyl group or a cycloalkylalkyl group having 3 to 8 carbon atoms in the cycloalkyl moiety, wherein in each case the cycloalkyl moiety may be substituted by a $C_{1-4}$-alkyl group or by a $C_{1-4}$-alkyl group and by 1 to 3 methyl groups, or $R_8$ denotes a bicycloalkyl or bicycloalkylalkyl group in which the bicycloalkyl moiety in each case contains 6 to 10 carbon atoms and additionally may be substituted by 1 to 3 methyl groups, or $R_8$ denotes an indanyl or cinnamyl group, or F denotes an $R_9CO$—O—$CHR_6$—O—CO— group wherein
$R_6$ denotes a hydrogen atom, an alkyl group, a phenyl group or a cycloalkyl group having 5 to 7 carbon atoms and
$R_9$ denotes a $C_{1-5}$-alkyl group, a $C_{1-4}$-alkoxy group, or a phenyl or $C_{5-7}$-cycloalkyloxy group;

the tautomers thereof, stereoisomers including the mixtures thereof, and the salts thereof, and the new intermediate products of general formula (Ia) wherein B to F are as hereinbefore defined and $R_{10}$ denotes an alkyl group, whilst unless otherwise specified the above-mentioned alkyl, alkylene or alkoxy moieties may each contain 1 to 3 carbon atoms.

Particularly preferred compounds of the above general formula I are those wherein $Y_1$ denotes a nitrogen atom or a carbon atom substituted by a group $R_1$, wherein
$R_1$ denotes a hydrogen atom or a methyl or ethyl group;

$Y_2$ denotes a nitrogen atom substituted by a group $R_1$, wherein $R_1$ is as hereinbefore defined, or $Y_2$ denotes an oxygen or sulphur atom;

A denotes a —CH=CH—N=CH—, —CH=N—CH=CH—, —$(CH_2)_2$—$NR_2$—$CH_2$— or —$(CH_2)_2$—$NR_2$—$(CH_2)_2$— bridge, wherein
$R_2$ denotes a hydrogen atom, a methyl, ethyl, allyloxycarbonyl or trifluoromethylcarbonyl group or an alkoxycarbonyl group having a total of 2 to 5 carbon atoms;

B denotes a phenylene group optionally substituted by a fluorine, chlorine or bromine atom, or by a methyl or ethyl group, wherein additionally a methine group may be replaced by an N-atom, or B denotes a 1,4-cyclohexylene group, wherein a >CH— unit in the 1- or 4-position may be replaced by a nitrogen atom or the >CH— units in the 1- and 4-positions may each be replaced by a nitrogen atom, or B may denote a 1,3-piperidinylene group;

C denotes a —$CH_2$—, —$CH_2CH_2$— or —CO— group, a —$CH_2$—CO—or —$NR_4$—CO— group, wherein the carbonyl group in each case is bound to group D and $R_4$ denotes a hydrogen atom or a $C_{1-2}$-alkyl group, or C denotes a —$CH_2$—$NR_4$—, —$NR_4$—$CH_2$—, —O—$CH_2$— or —$CH_2$—O group, wherein the nitrogen or oxygen atom cannot be bound to a nitrogen atom of group B or D directly or via a single carbon atom and $R_4$ is as hereinbefore defined;

D denotes a 1,4-cyclohexylene group wherein the >CH— unit in the 1-position which is bound to group C may be replaced by a nitrogen atom, or D denotes an —NR$_5$-1,4-cyclohexylene group, wherein R$_5$ denotes a hydrogen atom or a methyl, ethyl or benzyl group;

E denotes a C$_{1-3}$-alkylene group or a bond; and

F denotes a carbonyl group substituted by an R$_8$O— group, or F denotes an R$_9$CO—O—CHR$_6$—O—CO— group wherein R$_6$ denotes a hydrogen atom or a methyl group, R$_8$ denotes a hydrogen atom or a C$_{1-5}$-alkyl group; and R$_9$ denotes a C$_{1-5}$-alkyl group or a methoxy or ethoxy group, and the new intermediate products of general formula (Ia) wherein B to F are as hereinbefore defined and R$_{10}$ denotes a methyl group;

particularly those compounds of general formula I wherein

Y$_1$ denotes a nitrogen atom;

Y$_2$ denotes an —NH group or a sulphur atom;

A denotes a —CH═CH—N═CH—, —(CH$_2$)$_2$—NR$_2$—CH$_2$— or —(CH$_2$)$_2$—NR$_2$—(CH$_2$)$_2$— bridge wherein R$_2$ denotes a hydrogen atom, a methyl, ethyl or trifluoromethylcarbonyl group or an alkoxycarbonyl group having a total of 2 to 5 carbon atoms;

B denotes an optionally methyl-substituted phenylene group or

B denotes a 1,4-cyclohexylene group wherein a >CH— unit in the 1- or 4-position may be replaced by a nitrogen atom or the >CH— units in the 1- and 4-positions may each be replaced by a nitrogen atom;

C denotes a —CO group;

D denotes a 1,4-cyclohexylene group, wherein the >CH— unit in the 1-position which is bound to group C may be replaced by a nitrogen atom, or D denotes an —NR$_5$-1,4-cyclohexylene group, wherein R$_5$ denotes a hydrogen atom or a methyl group;

E denotes a methylene group or a bond; and

F denotes a carbonyl group substituted by an R$_8$O— group, wherein

R$_8$ denotes a hydrogen atom or a C$_{1-5}$-alkyl group;

the tautomers thereof, the stereoisomers including mixtures thereof, and the salts thereof.

The following may be mentioned as particularly preferred compounds:

(a) 2-[4-[(trans-4-carboxy-cyclohexyl)-aminocarbonyl]-phenyl]-4,5,6,7-tetrahydro-thiazolo[5,4-c]pyridine, (b) 2-[4-[(trans-4-methoxycarbonyl-cyclohexyl)-aminocarbonyl]-phenyl]-4,5,6,7-tetrahydro-thiazolo[5,4-c]pyridine, (c) 2-[4-[(trans-4-carboxy-cyclohexyl)-aminocarbonyl]-phenyl]-4,5,7,8-tetrahydro-6H-thiazolo[4,5-d]azepine, (d) 2-[4-[(trans-4-methoxycarbonyl-cyclohexyl)-aminocarbonyl]-phenyl]-4,5,7,8-tetrahydro-6H-thiazolo[4,5-d]azepine, (e) 2-[1-[(trans-4-carboxy-cyclohexyl)-aminocarbonyl]-piperid-4-yl]-4,5,6,7-tetrahydro-thiazolo[5,4-c]-pyridine, (f) 2-[1-[(trans-4-carboxy-cyclohexyl)-aminocarbonyl]-piperid-4-yl]-4,5,7,8-tetrahydro-6H-thiazolo[4,5-d]azepine, (g) 2-[1-[(trans-4-methoxycarbonyl-cyclohexyl)-aminocarbonyl]-piperid-4-yl ]-4,5,7,8-tetrahydro-6H-thiazolo[4,5-d]azepine, (h) 2-[1-[(trans-4-isobutyloxycarbonyl-cyclohexyl)-aminocarbonyl]-piperid-4-yl]-4,5,7,8-tetrahydro-6H-thiazolo[4,5-d]azepine, (i) 2-[4-[(trans-4-carboxy-cyclohexyl)-aminocarbonyl]-2-methyl-phenyl]-4,5,6,7-tetrahydro-thiazolo[5,4-c]-pyridine, (j) 2-[4-[(trans-4-methoxycarbonyl-cyclohexyl)-aminocarbonyl]-2-methyl-phenyl ]-4,5,6,7-tetrahydro-thiazolo[5,4-c ]pyridine, (k) 2-[trans-4-[(trans-4-carboxy-cyclohexyl)-aminocarbonyl]-cyclohexyl]-4,5,7,8-tetrahydro-6H-thiazolo[4,5-d]azepine, (l) 2-[1-[(trans-4-ethoxycarbonyl-cyclohexyl)-aminocarbonyl]-piperid-4-yl]-4,5,7,8-tetrahydro-6H-thiazolo[4,5-d]azepine, (m) 2-[1-[(trans-4-isopropoxycarbonyl-cyclohexyl)-aminocarbonyl]-piperid-4-yl ]-4,5,7,8-tetrahydro-6H-thiazolo[4,5-d]azepine and the salts thereof.

The new compounds may be prepared, for example, using the following methods:

a) In order to prepare compounds of general formula I wherein R$_2$ represents a hydrogen atom or F represents a carboxy group or R$_2$ denotes a hydrogen atom and F denotes a carboxy group:

converting a compound of general formula

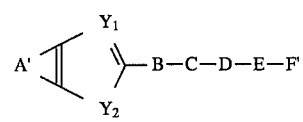

(wherein

B to E, Y$_1$ and Y$_2$ are as hereinbefore defined,

A' has the meanings given for A hereinbefore, except that additionally R$_2$ represents a group which may be cleaved by hydrolysis, treatment with an acid or base, thermolysis or hydrogenolysis, and F' denotes a carboxy group or a group which can be converted into a carboxy group by hydrolysis, treatment with an acid, thermolysis or hydrogenolysis, but at least one of the groups A' or F' must contain a group which can be cleaved by hydrolysis, treatment with acid, thermolysis or hydrogenolysis) into a compound of general formula I wherein R$_2$ denotes a hydrogen atom or F denotes a carboxyl group or R$_2$ denotes a hydrogen atom and F denotes a carboxy group.

For example, functional derivatives of the carboxyl group such as unsubstituted or substituted amides, esters, thioesters, trimethylsilylesters, orthoesters, iminoesters, amidines or anhydrides thereof, or a nitrile group may be converted by hydrolysis into a carboxyl group, esters with tertiary alcohols, e.g. the tert.butylester, may be converted by treatment with an acid or thermolysis into a carboxyl group and esters with aralkanols, e.g. the benzylesters, may be converted by hydrogenolysis into a carboxyl group and imino groups which are substituted by a protecting group such as formyl, acetyl, trifluoroacetyl, allyloxycarbonyl, ethoxycarbonyl, tert.butoxycarbonyl or benzyloxycarbonyl groups, may be converted into a free imino group by hydrolysis, imino groups substituted by a protecting group such as tert.butoxycarbonyl, benzyloxycarbonyl, benzyl, methoxybenzyl or 2,4-dimethoxybenzyl groups, may be converted into a free imino group by hydrogenolysis and imino groups substituted by a protecting group such as an allyloxycarbonyl group may be converted into a free imino group in the presence of a catalyst such as tetrakis-(triphenylphosphine)-palladium(O).

The hydrolysis is appropriately carried out either in the presence of an acid such as hydrochloric acid, sulphuric acid, phosphoric acid, acetic acid, trichloroacetic acid or trifluoroacetic acid or mixtures thereof, or in the presence of a base such as lithium hydroxide, sodium hydroxide or potassium hydroxide, in a suitable solvent such as water, water/methanol, water/ethanol, water/isopropanol, methanol, ethanol, water/tetrahydrofuran or water/dioxane, at temperatures between 31 10° and 120° C., e.g. at temperatures between ambient temperature and the boiling temperature of the reaction mixture.

If F' in a compound of formula II denotes a cyano or aminocarbonyl group, these groups may also be converted into a carboxyl group with a nitrite, e.g. sodium nitrite, in the presence of an acid such as sulphuric acid, whilst the latter is appropriately used as solvent at the same time, at temperatures between 0° and 50° C.

If for example in a compound of formula II A' contains or F' denotes a tert.butyloxycarbonyl group, the tert.butyl group may also be cleaved by treating with an acid such as trifluoroacetic acid, formic acid, p-toluenesulphonic acid, sulphuric acid, hydrochloric acid, phosphoric acid or polyphosphoric acid, optionally in an inert solvent such as methylene chloride, chloroform, benzene, toluene, diethylether, tetrahydrofuran or dioxane, preferably at temperatures between −10° C. and 120° C., e.g. at temperatures between 0° and 60° C., or thermally, optionally in an inert solvent such as methylene chloride, chloroform, benzene, toluene, tetrahydrofuran or dioxane and optionally in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 120° C.

If for example in a compound of formula II A' contains or F' denotes a benzyloxycarbonyl group, the benzyl group may also be hydrogenolytically cleaved in the presence of a hydrogenation catalyst such as palladium/charcoal, in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar.

If A' denotes an allyloxycarbonyl group in a compound of general formula II, the allyloxycarbonyl group is cleaved by treating with a catalytic amount of tetrakis-(triphenylphosphine)-palladium(O), preferably in a solvent such as tetrahydrofuran and preferably in the presence of an excess of a base such as morpholine or 1,3-dimedone, at temperatures between 0° and 100° C., preferably at ambient temperature and under inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane, at temperatures between 20° and 70° C.

b) In order to prepare compounds of general formula I wherein C denotes a —CO— or —CH$_2$CO— group:
Reacting a compound of general formula

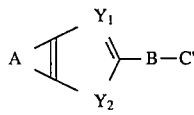  (III)

(wherein
A, B, Y$_1$ and Y$_2$ are as hereinbefore defined and C' denotes a carboxy or carboxymethyl group) with an amine of general formula

H—D—E—F  (IV)

wherein
D to F are as hereinbefore defined.

The reaction is conveniently carried out in a solvent or mixture of solvents such as methylene chloride, dimethylformamide, dimethylsulphoxide, benzene, toluene, chlorobenzene, tetrahydrofuran, benzene/tetrahydrofuran or dioxane, optionally in the presence of an acid such as hydrochloric acid or in the presence of a dehydrating agent, e.g. in the presence of isobutylchloroformate, thionylchloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N,-dicyclohexylcarbodiimide/N-hydroxysuccinimide, dimethylaminopyridine or 1-hydroxybenzotriazole, N,N'-carbonyldiimidazole or N,N'-thionyldiimidazole or triphenylphosphine/carbon tetrachloride, appropriately at temperatures between 0° and 150° C., preferably at temperatures between 0° and 50° C.

c) In order to prepare compounds of general formula I wherein C denotes a —CO— or —NR$_4$CO— group:
Reacting a compound of general formula

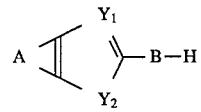  (V)

(wherein
A, B, Y$_1$ and Y$_2$ are as hereinbefore defined) with a compound of general formula

Z$_1$—C"—D—E—F  (VI)

wherein
D to F are as hereinbefore defined,
C" denotes a carbonyl group and
Z$_1$ denotes a leaving group such as a halogen atom, e.g.
a chlorine or bromine atom, or an optionally substituted phenoxy group, e.g. a p-nitro-phenoxy group.

The reaction is conveniently carried out in a solvent or mixture of solvents such as water, tetrahydrofuran, tetrahydrofuran/water, dioxane, dioxane/water, methylene chloride, chloroform, ethyl acetate or dimethylformamide, expediently in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvent, at temperatures between −30° and 150° C., but preferably at temperatures between −10° and 120° C.

d) In order to prepare compounds of general formula I wherein F denotes a carbonyl group substituted by an R$_8$'O group, wherein R$_8$' has the meanings given for R$_8$ hereinbefore, with the exception of the hydrogen atom:
Reacting a compound of general formula

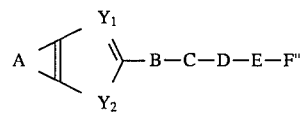  (VII)

(wherein
A to E, Y$_1$ and Y$_2$ are as hereinbefore defined and F" denotes a carboxy or alkoxycarbonyl group) with an alcohol of general formula

HO—R$_8$'      (VIII)

wherein

R$_8$' has the meanings given for R$_8$ hereinbefore with the exception of the hydrogen atom.

The reaction is conveniently carried out in a solvent or mixture of solvents such as methylene chloride, dimethylformamide, dimethylsulphoxide, benzene, toluene, chlorobenzene, tetrahydrofuran, benzene/tetrahydrofuran or dioxane, optionally in the presence of an acid such as hydrochloric acid or in the presence of a dehydrating agent, e.g. in the presence of isobutylchloroformate, thionylchloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, dimethylaminopyridine or 1-hydroxybenzotriazole, N,N'-carbonyldiimidazole or N,N'-thionyldiimidazole or triphenylphosphine/carbon tetrachloride, conveniently at temperatures between 0° and 150° C., preferably at temperatures between 0° and 50° C.

The reaction of a corresponding alkoxy compound of general formula VII with an alcohol of general formula X is preferably carried out in the relevant alcohol as solvent, optionally in the presence of another solvent such as methylene chloride or ether, preferably in the presence of an acid such as hydrochloric acid at temperatures between 0° and 100° C., preferably at temperatures between 20° and 80° C.

e) In order to prepare compounds of general formula I wherein F denotes a carbonyl group substituted by an R$_8$'O group, or F denotes an R$_9$CO—O—CHR$_6$—O—CO— group, wherein R$_6$ and R$_9$ are as hereinbefore defined and R$_8$' has the meanings given for R$_8$ hereinbefore, with the exception of the hydrogen atom:

Reacting a compound of general formula

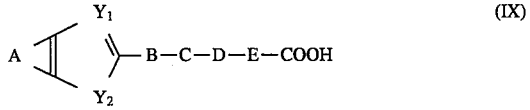      (IX)

(wherein

A to E, Y$_1$ and Y$_2$ are as hereinbefore defined) with a compound of general formula

      (X)

wherein

R$_{11}$ has the meanings given for R$_8$ hereinbefore, with the exception of the hydrogen atom, or R$_{11}$ represents an R$_9$CO—O—CHR$_6$— group, wherein R$_6$ and R$_9$ are as hereinbefore defined and Z$_2$ denotes a leaving group such as a halogen atom, e.g. a chlorine or bromine atom.

The reaction is conveniently carried out in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methyl-morpholine, which may simultaneously serve as solvent, or optionally in the presence of silver carbonate or silver oxide, at temperatures between −30° and 100° C., but preferably at temperatures between −10° and 80° C.

f) In order to prepare compounds of general formula I wherein R$_2$ denotes an alkoxycarbonyl group having a total of 2 to 5 carbon atoms or an alkyl, phenylalkyl, allyloxycarbonyl, phenylalkoxycarbonyl, trifluoromethylcarbonyl, R$_1$CO— or R$_3$CO—O—CHR$_1$—OCO— group:

Reacting a compound of general formula

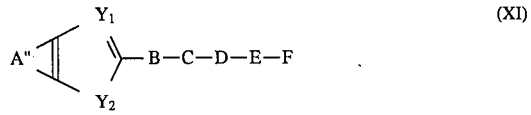      (XI)

(wherein

B to F, Y$_1$ and Y$_2$ are as hereinbefore defined and A" denotes an —N=CH—NH—(CH$_2$)$_m$—, —CH$_2$—NH—CH=N— or (CH$_2$)$_n$—NH—(CH$_2$)$_p$— bridge which in each case may be substituted in the carbon moiety by one or two alkyl groups, whilst p, m and n are as hereinbefore defined) with a compound of general formula

      (XII)

wherein

R$_2$' has the meanings given for R$_2$ hereinbefore, with the exception of the hydrogen atom, and Z$_3$ denotes a leaving group such as a halogen atom, e.g. a chlorine, bromine or iodine atom, or a sulphonic acid ester group, e.g. a methanesulphonyloxy or p-toluenesulphonyloxy group, or Z$_3$ together with an adjacent hydrogen atom of the group R$_2$' represents an oxygen atom.

The reaction is preferably carried out in a solvent such as methylene chloride, tetrahydrofuran, dioxane, dimethylsulphoxide or dimethylformamide, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methylmorpholine, which may simultaneously serve as solvent, or optionally in the presence of silver carbonate or silver oxide, at temperatures between −30° and 100° C., but preferably at temperatures between −10° and 80° C.

Alkylation with a compound of formula XII, wherein Z$_3$ denotes a leaving group, is conveniently carried out in a solvent such as methylene chloride, tetrahydrofuran, dioxane, dimethylsulphoxide or dimethylformamide, optionally in the presence of a base such as sodium carbonate, potassium carbonate or sodium hydroxide solution or in the presence of a tertiary organic base such as N-ethyl-diisopropylamine or N-methyl-morpholine, which may simultaneously serve as solvent, at temperatures between −30° and 100° C., but preferably at temperatures between −10° and 80° C.

The reductive alkylation with a carbonyl compound of general formula XII is carried out in the presence of a complex metal hydride such as sodium borohydride, lithium borohydride or sodium cyanoborohydride, appropriately at a pH from 6 to 7 and at ambient temperature or in the presence of a hydrogenation catalyst, e.g. with hydrogen in the presence of palladium/charcoal, at a hydrogen pressure of 1 to 5 bar. However, methylation is preferably carried out in the presence of formic acid as reducing agent at elevated temperatures, e.g. at temperatures between 60° and 120° C.

The acylation is conveniently carried out in a solvent such as tetrahydrofuran, methylene chloride, chloroform, dimethylformamide, water or mixtures of these solvents, optionally in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvent, at temperatures between −30° and 100° C., but preferably at temperatures between −10° and 60° C.

g) In order to prepare compounds of general formula I wherein A denotes a —CH$_2$—NR$_2$—(CH$_2$)$_2$— bridge (wherein R$_2$ is a hydrogen atom or has the meanings given for R$_{10}$ hereinbefore) and may be substituted in the carbon moiety by one or two alkyl groups, one of the groups Y$_1$ or Y$_2$ denotes a nitrogen atom and the other group Y$_1$ or Y$_2$ denotes an imino group:

Hydrogenation of a compound of general formula

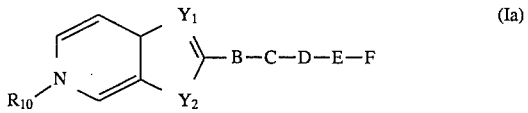

(Ia)

(wherein
B to F and R$_{10}$ are as hereinbefore defined).

The catalytic hydrogenation is preferably carried out in a suitable solvent such as methanol, methanol/water, acetic acid, ethyl acetate, ethanol, ether, tetrahydrofuran, dioxane or dimethylformamide, optionally with the addition of an acid such as hydrochloric acid in the presence of catalytically activated hydrogen, e.g. hydrogen in the presence of Raney nickel, platinum, rhodium or palladium/charcoal, at temperatures between 0° and 100° C., preferably at temperatures between 20° and 80° C.

In the reactions described hereinbefore, any reactive groups present such as hydroxy, carboxy, phosphono, O-alkylphosphono, amino, alkylamino, imino or amidino groups may be protected during the reaction by means of conventional protecting groups which are removed by cleaving after the reaction.

For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, the protecting group for a phosphono group may be an alkyl group such as methyl, ethyl, isopropyl or n-butyl or a phenyl or benzyl group, the protecting group for an optionally alkyl-substituted amidino group may be a benzyloxycarbonyl group and the protecting group for an amino, alkylamino or imino group may be a formyl, acetyl, trifluoroacetyl, allyloxycarbonyl, ethoxycarbonyl, tert.-butoxycarbonyl, benzyloxycarbonyl, benzyl, methoxybenzyl or 2,4-dimethoxybenzyl group and for the amino group a phthalyl group may also be considered.

The optional subsequent cleaving of a protecting group may, for example, be carried out hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or by ether cleaving, e.g. in the presence of iodotrimethylsilane, at temperatures between 0° and 120° C., preferably at temperatures between 10° and 100° C.

However, a benzyl, methoxybenzyl or benzyloxycarbonyl group may for example be cleaved hydrogenolytically, eg. using hydrogen in the presence of a catalyst such as palladium/charcoal in a solvent such as methanol, ethanol, ethyl acetate or glacial acetic acid, optionally with the addition of an acid such as hydrochloric acid, at temperatures between 0° and 100° C., but preferably at temperatures between 20° and 60° C., under a hydrogen pressure of 1 to 7 bar, preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid, or by treating with iodotrimethylsilane, optionally using a solvent such as methylene chloride, dioxane, methanol or ether.

A trifluoroacetyl group is preferably cleaved by treating with an acid such as hydrochloric acid, optionally in the presence of a solvent such as acetic acid, at temperatures between 50° and 120° C., or by treating with sodium hydroxide solution or aqueous lithium hydroxide solution, optionally in the presence of a solvent such as tetrahydrofuran or methanol at temperatures between 0° and 50° C.

An allyloxycarbonyl group is cleaved by treating with a catalytic amount of tetrakis-(triphenylphosphine)-palladium(O), preferably in a solvent such as tetrahydrofuran and preferably in the presence of an allyl group acceptor such as morpholine or 1,3-dimedone, at temperatures between 0° and 100° C., preferably at ambient temperature and under inert gas, or by treating with a catalytic amount of tris-(triphenylphosphine)-rhodium(I)chloride, in a solvent such as aqueous ethanol and optionally in the presence of a base such as 1,4-diazabicyclo[2.2.2]octane, at temperatures between 20° and 70° C.

A phthalyl group is preferably cleaved in the presence of hydrazine or a primary amine such as methylamine, ethylamine or n-butylamine in a solvent such as methanol, ethanol, isopropanol, toluene/water or dioxane, at temperatures between 20° and 50° C.

The cleaving of only one alkyl group from an O,O'-dialkylphosphono group is carried out for example with sodium iodide in a solvent such as acetone, ethylmethylketone, acetonitrile or dimethylformamide, at temperatures between 40° and 150° C., but preferably at temperatures between 60° and 100° C.

The cleaving of both alkyl groups from an O,O'-dialkylphosphono group is carried out, for example, with iodotrimethylsilane, bromotrimethylsilane or chlorotrimethylsilane/sodium iodide in a solvent such as methylene chloride, chloroform or acetonitrile at temperatures between 0° C. and the boiling temperature of the reaction mixture, but preferably at temperatures between 20° and 60° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (see Allinger N. L. and Eliel E. L. in "Topics in Stereochemistry", Vol. 6, Wiley Interscience, 1971) into their optical antipodes, and compounds of general formula I having at least 2 stereogenic centres may be separated on the basis of their physical-chemical differences using known methods, e.g. by chromatography and/or fractional crystallisation, into the diastereomers thereof, which, if they occur in racemic form, may subsequently be separated into the enantiomers as mentioned above.

The separation of enantiomers is preferably effected by column separation on chiral phases or by recrystallisation from an optically active solvent or by reacting with optically active substances (especially acids and the activated derivatives thereof or alcohols), which form salts or derivatives such as esters or amides with the racemic compound, and separation of the diastereomeric salt mixture or derivative thus obtained, e.g. on the basis of their different solubilities, whilst the free antipodes may be released from the pure diastereomeric salts by the action of suitable agents. Particularly useful, optically active acids include, for example, the D- and L-forms of tartaric acid, and dibenzoyltartaric acid, di-o-tolyl tartaric acid, malic acid, mandelic acid, camphorsulphonic acid, glutamic acid, aspartic acid and quinic acid. Examples of optically active alcohols include for example (+)- or (−)-menthol and examples of optically active acyl groups in amides include, for example, (+)- or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, acetic acid, fumaric acid, succinic acid, lactic acid, citric acid, tartaric acid or maleic acid.

In addition, the new compounds of formula I thus obtained, if they contain a carboxyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, arginine, cyclohexylamine, ethanolamine, diethanolamine and triethanolamine.

The compounds used as starting materials are known from the literature in some cases or may be obtained by methods known from the literature (see the Examples), for example by cyclising a corresponding o-pyridyldiamine with a corresponding carboxylic acid derivative or by reacting a corresponding carboxylic acid derivative with a corresponding 3-halo-piperid-4-one or 5-halo-azepin-4-one. A bicyclic derivative thus obtained can subsequently be converted into a desired starting compound by hydrolysis, alkylation and/or acylation.

A compound of general formula Ia is prepared by alkylating a corresponding benzimidazole of general formula I with a corresponding alkyl or phenylalkylhalide such as methyliodide or benzylbromide in a solvent such as dimethylsulphoxide and in the presence of a base such as potassium tert.butoxide at temperatures between 0° and 50° C., preferably at ambient temperature.

As already mentioned, the new bicyclic heterocyclic compounds of general formula I and the addition salts thereof, particularly the physiologically acceptable addition salts thereof with inorganic or organic acids or bases, have valuable properties. Thus, the new compounds of general formula I, wherein A contains a basic group or a group which may optionally be converted into a basic group in vivo and F represents a carboxyl, phosphono or O-alkylphosphono group or a group which can optionally be converted in vivo into a carboxyl, phosphono or O-alkylphosphono group, e.g. a carbonyl group substituted by an alkoxy or cycloalkoxy group, have valuable pharmacological properties, and in addition to having an inhibitory effect on inflammation and bone degradation, they have in particular antithrombotic, antiaggregatory and tumour- or metastasis-inhibiting effects.

By way of example, the compounds of general formula I were investigated for their biological effects as follows:

1. Inhibition of binding of $^3$H-BIBU 52 to human thrombocytes:

A suspension of human thrombocytes in plasma is incubated with $^3$H-BIBU 52 [=(3S,5S)-5-[(4'-amidino-4-biphenylyl)oxymethyl]-3-[(carboxyl)methyl]-2pyrrolidinone[3-$^3$H-4-biphenylyl]] (see German Patent Application P 42 14 245.8 of the same applicant, dated 30.04.1992, internal reference: Case 5/1093-FL), which replaces the $^{125}$I fibrinogen ligand known from the literature, and various concentrations of the substance to be tested. The free and bound ligand are separated by centrifuging and quantified by scintillation counting. The inhibition of $^3$H-BIBU 52 binding by the test substance is determined from the measurements obtained.

In order to do this, donor blood is taken from an anticubital vein and anticoagulated with trisodium citrate (final concentration 13 mM). The blood is centrifuged for 10 minutes at 170×g and the supernatant platelet-rich plasma (PRP) is removed. The remaining blood is vigorously centrifuged once more in order to obtain plasma. The PRP is diluted 1:10 with autologous plasma. 750 µl are incubated with 50 µl of physiological saline solution, 100 µl of test substance solution, 50 µl of $^{14}$C-sucrose (3,700 Bq) and 50 µl of $^3$H-BIBU 52 (final concentration: 5 nM) at ambient temperature for 20 minutes. In order to measure the non-specific binding, 5 µl of BIBU 52 (final concentration: 30 µM) are used instead of the test substance. The samples are centrifuged for 20 seconds at 10,000× g and the supernatant is poured off. 100 µl thereof are measured in order to determine the free ligand. The pellet is dissolved in 500 µl of 0.2N NaOH, 450 µl are mixed with 2 ml of scintillator and 25 µl of 5N HCl and measured. The residual plasma remaining in the pellet is determined from the $^{14}$C-content and the bound ligand is determined from the $^3$H-measurement. After the non-specific binding has been deducted, the pellet activity is plotted against the concentration of the test substance and the concentration for a 50% inhibition of binding is determined.

2. Antithrombotic activity
Method

The thrombocyte aggregation is measured using the method of Born and Cross (J. Physiol. 170:397 (1964)) in platelet-rich plasma taken from healthy volunteers. To inhibit coagulation, the blood is mixed with 3.14% sodium citrate in a volume ratio of 1:10.
Collagen-induced aggregation The pattern of the decrease in optical density of the platelet suspension is photometrically measured and recorded after the addition of the aggregation-triggering substance. The rate of aggregation is determined from the angle of inclination of the density curve. The point on the curve where there is maximum light transmittance is used to calculate the optical density.

The concentration of collagen used is as small as possible but sufficient to produce an irreversible reaction curve. Standard commercial collagen produced by Hormonchemie of Munich is used.

Before the addition of the collagen the plasma is incubated for 10 minutes at 37° C. with the substance.

From the measurements obtained, the $EC_{50}$ is determined graphically as the concentration giving a 50% change in the optical density in terms of the inhibition of aggregation.

The following table shows the results which were obtained:

| Substance (Example No.) | Competitive binding of $^3$H-BIBU 52/test substance to human thrombocytes IC$_{50}$ [nM] | Inhibition of platelet aggregation EC$_{50}$ [nM] |
| --- | --- | --- |
| 2(1) | 210 | 2600 |
| 2(4) | 450 | 1440 |
| 3(5) | 31 | 100 |
| 3(6) | 42 | 100 |
| 3(8) | 2100 | 4200 |
| 3(12) | 2000 | 2900 |
| 4 | 96 | 410 |
| 4(1) | 75 | 680 |
| 4(3) | 24 | 220 |
| 4(4) | 120 | 110 |
| 7 | 1600 | 660 |
| 7(1) | 1400 | 1400 |
| 7(2) | 1300 | 2600 |
| 7(3) | 1500 | 1300 |

The compounds according to the invention are well tolerated because after intravenous administration of 30 mg/kg of the compounds of Examples 4 and 4(1) to three mice in each case, no animals died.

In the light of their inhibitory effect on cell-cell or cell-matrix interactions, the new cyclic urea derivatives of general formula I and the physiologically acceptable addition salts thereof are suitable for combating or preventing diseases in which smaller or greater cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above, the dosage is between 0.1 μg and 30 mg/kg of body weight, preferably 1 μg to 15 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, -receptor antagonists, alkylnitrates such as glycerol trinitrate, phospho-diesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudine, inhibitors of thrombin or other activated clotting factors, may be incorporated together with one or more inert conventional carriers and/or diluents, e.g. corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

Preparation of the starting compounds:

EXAMPLE I

Ethyl 4-(aminothiocarbonyl)-benzoate

Hydrogen sulphide is piped through a solution of 15.0 g of ethyl 4-cyano-benzoate in 100 ml of pyridine and 12 ml of triethylamine for 2 hours. After 2 hours' stirring at ambient temperature hydrogen sulphide is piped through for a further hour. The mixture is stirred for 2 days at ambient temperature. The solution is diluted with 1 liter of water and the precipitate is suction filtered and dried.

Yield: 16.3 g (91% of theory), $R_f$ value: 0.36 (silica gel; methylene chloride/methanol =19:1)

The following compounds are obtained analogously to Example I:

(1) methyl 3-(aminothiocarbonyl)-benzoate $R_f$ value: 0.65 (silica gel; ethyl acetate/cyclohexane=1:1)

(2) methyl 4-(aminothiocarbonyl)-3-methyl-benzoate $R_f$ value: 0.56 (silica gel; ethyl acetate/cyclohexane=1:1)

(3) ethyl trans-4-(aminothiocarbonyl)-cyclohexanecarboxylate

The solvent is evaporated off under reduced pressure and the residue is triturated with ether and suction filtered. $R_f$ value: 0.29 (silica gel; methylene chloride/methanol =19:1)

EXAMPLE II 2-(4-Ethoxycarbonyl-phenyl)-4,5,6,7-tetrahydro-thiazolo-[5,4-c]pyridine-hydrobromide A solution of 10.65 g of 3-bromo-piperidin-4-one-hydrobromide and 8.6 g of ethyl 4-(aminothiocarbonyl)-benzoate in 50 ml of dimethylformamide is heated to 100° C. for 9 hours. Then the solvent is largely evaporated off under reduced pressure and the crude product is distributed between water and ethyl acetate. The precipitate which forms between the phases is suction filtered and dried.

Yield: 3.0 g (20% of theory), $R_f$ value: 0.19 (silica gel; methylene chloride/methanol =9:1)

The ethyl acetate phase is separated off and the aqueous phase is neutralised with sodium hydrogen carbonate. After extraction of the aqueous phase with ethyl acetate the organic phase is dried and the solvent is evaporated down under reduced pressure. A further 1.4 g of product are obtained (12% of theory) in the form of the free base.

The following compounds are obtained analogously to Example II:

(1) 2-(4-ethoxycarbonyl-phenyl)-4,5,7,8-tetrahydro-6H-thiazolo[4,5-d]azepine 5-Bromo-azepin-4-one-hydrobromide is used. The solution is heated to 120° C. for 3 hours. It is then diluted with ethyl acetate and the precipitate is suction filtered. The precipitate is dissolved in water. The aqueous solution is mixed with conc. ammonia until an alkaline reaction mixture is obtained and then extracted with ethyl acetate. The organic phase is dried and the solvent is evaporated off under reduced pressure. $R_f$ value: 0.32 (silica gel; methylene chloride/methanol/conc. ammonia=8:2:0.2)

(2) 2-(3-methoxycarbonyl-phenyl)-4,5,7,8-tetrahydro-6H-thiazolo[4,5-d]azepine 5-Bromo-azepin-4-one-hydrobromide is used. The solution is heated over a steam bath for 3 hours and subsequent working up is carried out analogously to Example II(1). $R_f$ value: 0.04 (silica gel; methylene chloride/methanol/conc. ammonia= 9:1:0.1)

(3) 2-(1-benzyloxycarbonyl-piperid-4-yl)-4,5,6,7-tetrahydro-thiazolo[5,4-c]pyridine The crude product is chromatographed over silica gel. $R_f$ value: 0.18 (silica gel; methylene chloride/methanol=9:1)

(4) 2-(1-benzyloxycarbonyl-piperid-4-yl)-4,5,7,8-tetrahydro-6H-thiazolo[4,5-d]azepine The crude product is chromatographed over silica gel. $R_f$ value: 0.32 (silica gel; methylene chloride/methanol/conc. ammonia= 9:1:0.1)

(5) 2-(4-methoxycarbonyl-2-methyl-phenyl)-4,5,6,7-tetrahydro-thiazolo[5,4-c]pyridine-hydrobromide $R_f$ value: 0.45 (silica gel; methylene chloride/methanol/ conc. ammonia=9:1:0.1)

(6) 2-(4-ethoxycarbonyl-cyclohexyl)-4,5,7,8-tetrahydro-6H-thiazolo[4,5-d]azepine 5-Bromo-azepin-4-one-hydrobromide is used. It is worked up analogously to Example II(1). $R_f$ value: 0.22 (silica gel; methylene chloride/methanol/conc. ammonia=9:1:0.1)

EXAMPLE III 5-tert.Butyloxycarbonyl-2-(4-ethoxycarbonyl-phenyl)-4,5,6,7-tetrahydro-thiazolo[5,4-c]pyridine 1.59 g of di-tert.butyl-pyrocarbonate are added to a suspension of 2.70 g of 2-(4-ethoxycarbonyl-phenyl)-4,5,6,7-tetrahydro-thiazolo[5,4-c]pyridine-hydrobromide and 1.0 ml of triethylamine in 100 ml of acetonitrile and the solution is stirred at ambient temperature for 2 hours. The solvent is then evaporated down under reduced pressure and the residue is distributed between water and ethyl acetate. The ethyl acetate phase is washed with water and dilute saline solution. The organic phase is dried and the solvent is evaporated off under reduced pressure.

Yield: 2.8 g (quantitative) $R_f$ value: 0.42 (silica gel; methylene chloride/methanol=19:1)

The product reacted in Example IV without being purified.

The following compounds are obtained analogously to Example III:

(1) 6-tert.butyloxycarbonyl-2-(4-ethoxycarbonyl-phenyl)-4,5,7,8-thiazolo[4,5-d]azepine $R_f$ value: 0.34 (silica gel; methylene chloride/methanol=30:1)

(2) 6-tert.butyloxycarbonyl-2-(3-methoxycarbonyl-phenyl)-4,5,7,8-thiazolo[4,5-d]azepine $R_f$ value: 0.40 (silica gel; methylene chloride/methanol=19:1)

(3) 5-tert.butyloxycarbonyl-2-(4-methoxycarbonyl-2-methyl-phenyl)- 4,5,6,7-tetrahydro-thiazolo[5,4-c]-pyridine $R_f$ value: 0.51 (silica gel; methylene chloride/ methanol=19:1)

(4) 6-tert.butyloxycarbonyl-2-(4-ethoxycarbonyl-cyclohexyl)-4,5,7,8-thiazolo[4,5-d]azepine The crude product is purified by chromatography. A mixture of the cis- and trans- isomers is obtained which is reacted in Example IV(5). $R_f$ value: 0.51 and 0.62 (silica gel; methylene chloride/methanol=30:1; developed three times)

EXAMPLE IV 5-tert.Butyloxycarbonyl-2-(4-carboxy-phenyl)-4,5,6,7-tetrahydro-thiazolo[5,4-c]pyridine A solution of 1.35 g of 5-tert.butyloxycarbonyl-2-(4-ethoxycarbonyl-phenyl)-4,5,6,7-tetrahydro-thiazolo[5,4-c] pyridine and 3.8 ml of a 1.4 molar lithium hydroxide solution in 20 ml of tetrahydrofuran and 10 ml of methanol is stirred at ambient temperature for 16 hours. Then it is neutralised with 5.3 ml of 1N hydrochloric acid and diluted with water. The precipitate is suction filtered. By evaporating the mother liquor under reduced pressure and subsequently suction filtering the precipitate, further product is obtained.

Yield: 1.20 g (87% of theory), $R_f$ value: 0.40 (silica gel; methylene chloride/methanol=9:1)

The following compounds are obtained analogously to Example IV:

(1) 6-tert.butyloxycarbonyl-2-(4-carboxy-phenyl)- 4,5,7,8-tetrahydro-thiazolo[4,5-d]azepine $R_f$ value: 0.42 (silica gel; methylene chloride/methanol=9:1)

(2) 6-tert.butyloxycarbonyl-2-(3-carboxy-phenyl)-4,5,7,8-tetrahydro-thiazolo[4,5-d]azepine $R_f$ value: 0.46 (silica gel; methylene chloride/methanol=9:1)

(3) 2-(4-carboxy-phenyl)-5-methyl-imidazo[4,5-d] azepine After neutralisation of the reaction solution with 1N hydrochloric acid it is evaporated to dryness under reduced pressure. The residue is dissolved in water. Crystallisation sets in after the addition of methanol. $R_f$ value: 0.24 (silica gel; n-butanol/acetic acid/water=4:1:1)

(4) 5-tert.butyloxycarbonyl-2-(4-carboxy-2-methyl-phenyl)-4,5,6,7-tetrahydro-thiazolo[5,4-c]pyridine $R_f$ value: 0.38 (silica gel; methylene chloride/methanol= 9:1)

(5) 6-tert.butyloxycarbonyl-2-(trans-4-carboxy-cyclohexyl)-4,5,7,8-tetrahydro-thiazolo[4,5-d]azepine The reaction solution is neutralised with citric acid, excess solvent is eliminated under reduced pressure and the aqueous phase is extracted with ethyl acetate. After the organic phase has been dried over magnesium sulphate the solvent is evaporated off under reduced pressure and the residue is chromatographed over silica gel. $R_f$ value: 0.31 (silica gel; methylene chloride/methanol= 19:1; developed three times)

EXAMPLE V

1-Benzyloxycarbonyl-piperid-4-yl-carboxylic acid amide 39 ml of 1N sodium hydroxide solution are slowly added dropwise to a solution of 5.0 g of piperid-4-yl-carboxylic acid amide and 5.54 ml of benzylchloroformate in 30 ml of water and 40 ml of acetone so as to keep the pH constant at between 6 and 8. The mixture is stirred for one hour at ambient temperature. Then the acetone is evaporated off under reduced pressure and the precipitate is suction filtered and dried.

Yield: 8.8 g (86% of theory), $R_f$ value: 0.55 (silica gel; methylene chloride/methanol/conc. ammonia=9:1:0.1)

EXAMPLE VI

1-Benzyloxycarbonyl-piperid-4-yl-thiocarboxylic acid amide

A solution of 8.7 g of 1-benzyloxycarbonyl-piperid-4-yl-carboxylic acid amide and 8.0 g of 2,4-bis-(4-methoxyphenyl)-1,3-dithia-2,4-diphosphetan-2,4-disulphide in 150 ml of tetrahydrofuran is stirred at ambient temperature for 4 hours. The solvent is evaporated off under reduced pressure and the residue is chromatographed over silica gel.

Yield: 7.7 g (83% of theory), $R_f$ value: 0.59 (silica gel; methylene chloride/methanol=9:1)

EXAMPLE VII 2-(1-Benzyloxycarbonyl-piperid-4-yl)-6-trifluoroacetyl-4,5,7,8-tetrahydro-thiazolo[4,5-d]azepine A solution of 1.6 g of 2-(1-benzyloxycarbonyl-piperid-4-yl)-4,5,7,8-tetrahydro-6H-thiazolo[4,5-d]azepine, 0.9 ml of triethylamine and 0.9 ml of trifluoroacetic acid anhydride in 50 ml of methylene chloride is stirred at ambient temperature for 16 hours. The solution is then washed with water, with 0.5N hydrochloric acid and with dilute sodium hydrogen carbonate solution. The organic phase is dried over magnesium sulphate and the solvent is evaporated off under reduced pressure.

Yield: 1.9 g (94% of theory), $R_f$ value: 0.35 (silica gel; methylene chloride/methanol=19:1)

The following compound is obtained analogously to Example VII:

(1) 2-(1-benzyloxycarbonyl-piperid-4-yl)-5-trifluoroacetyl-4,5,6,7-tetrahydro-thiazolo[5,4-c]pyridine $R_f$ value: 0.64 (silica gel; methylene chloride/methanol=9:1)

EXAMPLE VIII

6-Trifluoroacetyl-2-(piperid-4-yl)-4,5,7,8-tetrahydro-thiazolo[4,5-d]azepine-dihydrobromide A solution of 1.9 g of 2-(1-benzyloxycarbonyl-piperid-4-yl)-6-trifluoroacetyl-4,5,7,8-tetrahydro-thiazolo[4,5-d]azepine in 10 ml of acetic acid and 10 ml of 35% hydrogen bromide in acetic acid is stirred at 15° C. for 3 hours. Ether is added and the mixture is decanted. This operation is repeated several times and the mixture is suction filtered. The product is dried over potassium hydroxide in a desiccator.

Yield: 1.9 g of hygroscopic product (94% of theory), $R_f$ value: 0.27 (silica gel; methylene chloride/methanol/conc. ammonia=8:2:0.2)

The following compounds are obtained analogously to Example VIII:

(1) 5-trifluoroacetyl-2-(1-piperid-4-yl)-4,5,6,7-tetrahydro-thiazolo[5,4-c]pyridine-dihydrobromide $R_f$ value: 0.38 (silica gel; methylene chloride/methanol/conc. ammonia=8:2:0.2)

(2) 6-methyl-2-(piperid-4-yl)-4,5,7,8-tetrahydro-thiazolo[4,5-d]azepine-trihydrobromide $R_f$ value: 0.24 (silica gel; methylene chloride/methanol/conc. ammonia=7:3:0.5)

EXAMPLE IX 2-(4-Methoxycarbonyl-phenyl)-1H-imidazo-[4,5-c]pyridine 16.9 g of monomethyl-terephthalate and 10.3 g of 3,4-diamino-pyridine in 50 ml of phosphorusoxychloride are stirred for 16 hours at 120° C. A further 50 ml of phosphorusoxychloride are added and the mixture is stirred for 8 hours at 120° C. The viscous crude product, still hot, is poured into an ice/water mixture with vigorous stirring and the crystalline residue is suction filtered. The crystals are stirred with dilute ammonia solution and suction filtered once more (1st crystals). The mother liquor is neutralised with concentrated ammonia (pH 7–8) and the precipitate is suction filtered (2nd crystals). The combined crystals 1 and 2 are triturated with acetone and suction filtered.

Yield: 2.0 g (79% of theory), $R_f$ value: 0.36 (silica gel; methylene chloride/methanol=9:1)

EXAMPLE X 2-(4-Carboxy-phenyl)-1H-imidazo[4,5-c]pyridine 23 g of 2-(4-methoxycarbonyl-phenyl)-1H-imidazo[4,5-c]pyridine in 200 ml of 6N hydrochloric acid are heated to 100° C. for 4 hours. The precipitate is suction filtered over a G2 frit, then suspended in water and made alkaline with concentrated ammonia. In order to remove any insoluble components the mixture is suction filtered over kieselguhr and the aqueous solution is neutralised with acetic acid. The crystalline residue is suction filtered and washed with water, acetone and ether.

Yield: 14.0 g (64% of theory), $R_f$ value: 0.33 (Reversed Phase RP18, methanol/5% sodium chloride solution=6:4)

EXAMPLE XI 2-(4-Methoxycarbonyl-phenyl)-5-methyl-5H-imidazo[5,4-c]-pyridine 2.2 g of potassium tert.butoxide are added to 5.0 g of 2-(4-carboxy-phenyl)-1H-imidazo[4,5-c]pyridine in 200 ml of dimethylsulphoxide and the mixture is stirred for one hour at ambient temperature. 1.3 ml of methyl iodide are added dropwise thereto and stirring is continued for a further hour. Then 2.2 g of potassium tert.butoxide are added, the mixture is stirred for 30 minutes at ambient temperature, a further 1.3 ml of methyl iodide are added and stirring is continued for one more hour. The suspension is diluted with water. The product which crystallises out is suction filtered and dried.

Yield: 2.5 g (47% of theory), $R_f$ value: 0.09 (silica gel; ethyl acetate/methanol=9:1)

EXAMPLE XII 2-(1-Benzyloxycarbonyl-piperid-4-yl)-6-methyl-4,5,7,8-tetrahydro-thiazolo[4,5-d]azepine A solution of 9.0 g of 2-(1-benzyloxycarbonyl-piperid-4-yl)-4,5,7,8-tetrahydro-6H-thiazolo[4,5-d]azepine and 1.25 g of a 33% aqueous formaldehyde solution in 50 ml of acetic acid are heated to 100° C. for 30 minutes with the development of gas. Then the excess acetic acid is evaporated off and the residue is dissolved in water. The aqueous phase is neutralised with sodium hydrogen carbonate and extracted with ethyl acetate. The ethyl acetate phase is washed with water, dried over magnesium sulphate and the solvent is evaporated off under reduced pressure. An oil is obtained which is reacted according to Example VIII without further purification.

Yield: 8.8 g (94% of theory), $R_f$ value: 0.45 (silica gel; methylene chloride/methanol/conc. ammonia=9:1:0.1)

EXAMPLE XIII

Methyl 4-cyano-3-methyl-benzoate

A suspension of 25 g of methyl 4-bromo-3-methyl-benzoate and 11.2 g of copper cyanide in 50 ml of dimethylformamide is refluxed for 16 hours. The reaction solution is poured onto water and the aqueous phase is extracted several times with ethyl acetate. The organic phase is washed with water, dried over magnesium sulphate and the solvent is evaporated down under reduced pressure. The residue is chromatographed over silica gel with methylene chloride.

Yield: 6.2 g (31% of theory), $R_f$ value: 0.33 (silica gel; cyclohexane/ethyl acetate=7:3)

EXAMPLE XIV

Ethyl trans-4-carbamoyl-cyclohexanecarboxylate

A solution of 10 g of ethyl trans-4-carboxy-cyclohexanecarboxylate in 30 ml of thionylchloride is stirred at ambient temperature for 2 hours. Excess thionylchloride is evaporated off under reduced pressure and the residue is dissolved in ether. A concentrated ammonia solution is added dropwise to this solution at 0° C. The precipitate formed is suction filtered, then dissolved in methylene chloride and the solution is dried over magnesium sulphate. The solvent is evaporated off under reduced pressure.

Yield: 9.0 g (90% of theory), $R_f$ value: 0.45 (silica gel; methylene chloride/methanol/conc. ammonia=9:1:0.1)

EXAMPLE XV

Ethyl trans-4-cyano-cyclohexanecarboxylate

A solution of 9.0 g of ethyl trans-4-carbamoyl-cyclohexanecarboxylate, 14.8 g of triphenylphosphine, 6.3 ml of triethylamine and 4.8 ml of carbon tetrachloride in 100 ml of chloroform is refluxed for 16 hours. 11.0 g of triphenylphosphine are added and the mixture is refluxed for a further 5 hours. The solvent is evaporated off under reduced pressure and the residue is chromatographed over silica gel using methylene chloride as eluant.

Yield: 7.0 g (86% of theory), $R_f$ value: 0.44 (silica gel; methylene chloride) Preparation of the end compounds:

Example 1

5-tert.Butyloxycarbonyl-2-[4-[(trans-4-methoxycarbonyl-cyclohexyl)-aminocarbonyl]-phenyl]-4,5,6,7-tetrahydro-thiazolo[5,4-c]pyridine 1.11 g of N,N'-carbonyl-diimidazole is added to a suspension of 2.50 g of 5-tert.butyloxycarbonyl-2-(4-carboxy-phenyl]-4,5,6,7-tetrahydro-thiazolo[5,4-c]pyridine in 50 ml of tetrahydrofuran and the mixture is stirred for 3 hours at ambient temperature. Then a solution of 1.34 g of methyl trans-4-amino-cyclohexanecarboxylate-hydrochloride and 1.0 ml of triethylamine in 10 ml of tetrahydrofuran is added and the mixture is stirred for 5 days at ambient temperature. The solvent is evaporated off and the residue is distributed between water and methylene chloride. The methylene chloride phase is washed with sodium hydrogen carbonate solution and water, then dried and evaporated down. The residue is filtered with methylene chloride/methanol (19:1) over a little silica gel. The filtrate is evaporated down, the solids are triturated with ether and suction filtered.

Yield: 2.60 g (75% of theory), $R_f$ value: 0.75 (silica gel; methylene chloride/methanol=9:1) Mass spectrum: $M^+$=499

The following compounds are obtained analogously to Example 1:

(1) 5-tert.butyloxycarbonyl-2-[4-[4-(methoxycarbonylmethyl)-piperidinocarbonyl]-phenyl]-4,5,6,7-tetrahydro-thiazolo[5,4-c]pyridine Methyl piperid-4-yl-acetate-hydrochloride is used as the amine component. $R_f$ value: 0.66 (silica gel; methylene chloride/methanol=9:1) Mass spectrum: $M^+$=499

(2) 6-tert.butyloxycarbonyl-2-[4-[(trans-4-methoxycarbonyl-cyclohexyl)-aminocarbonyl]-phenyl]-4,5,6,7-tetrahydro-thiazolo[4,5-d]azepine $R_f$ value: 0.54 (silica gel; methylene chloride/methanol=9:1) Mass spectrum: $M^+$=513

(3) 6-tert.butyloxycarbonyl-2-[3-[(trans-4-methoxycarbonyl-cyclohexyl)-aminocarbonyl]-phenyl]-4,5,7,8-tetrahydro-thiazolo[4,5-d]azepine $R_f$ value: 0.64 (silica gel; methylene chloride/methanol/conc. ammonia=9:1:0.1) Mass spectrum: $M^+$=513

(4) 2-[4-[4-(methoxycarbonylmethyl)-piperidinocarbonyl]-phenyl]-1H-imidazo[4,5-c]pyridine Methyl piperid-4-yl-acetate-hydrochloride is used as the amine component. $R_f$ value: 0.24 (silica gel; methylene chloride/methanol=9:1)

(5) 2-[4-[(trans-4-methoxycarbonyl-cyclohexyl)-aminocarbonyl]-phenyl]-1H-imidazo[4,5-c]pyridine $R_f$ value: 0.58 (silica gel; methylene chloride/methanol/acetic acid=8:2:0.2) Mass spectrum: $M^+$=378

(6) 2-[4-[(trans-4-methoxycarbonyl-cyclohexyl)-aminocarbonyl]-phenyl]-5-methyl-imidazo[5,4-c]pyridine $R_f$ value: 0.13 (silica gel; methylene chloride/methanol=9:1) Mass spectrum: $M^+$=392

(7) 5-tert.butyloxycarbonyl-2-[4-[(trans-4-methoxycarbonyl-cyclohexyl)-aminocarbonyl]-2-methyl-phenyl]-4,5,6,7-tetrahydro-thiazolo[5,4-c]pyridine Melting point: from 155° C. (sintering) $R_f$ value: =0.49 (silica gel; methylene chloride/methanol=9:1)

(8) 6-tert.butyloxycarbonyl-2-[trans-4-[(trans-4-methoxycarbonyl-cyclohexyl)-aminocarbonyl]-cyclohexyl]-4,5,7,8-tetrahydro-thiazolo[4,5-d]azepine Melting point: from 215° C. (sintering) $R_f$ value: =0.66 (silica gel; methylene chloride/methanol=9:1) Mass spectrum: $M^+$=519

Example 2

2-[4-[(trans-4-Methoxycarbonyl-cyclohexyl)-aminocarbonyl]-phenyl]-4,5,6,7-tetrahydro-thiazolo[5,4-c]pyridine-hydrochloride Hydrogen chloride is piped through a solution of 1.0 g of 5-tert.butyloxycarbonyl-2-[4-[(trans-4-methoxycarbonyl-cyclohexyl)-aminocarbonyl]-phenyl]-4,5,6,7-tetrahydro-thiazolo[5,4-c]pyridine in 50 ml of dioxane for 15 minutes. After stirring at ambient temperature for 16 hours, methylene chloride is added until the precipitate has completely dissolved. After the addition of ether saturated with hydrogen chloride, the mixture is stirred for a further 2 hours at ambient temperature. Then the solvent is eliminated under reduced pressure, the residue remaining is triturated with ether and suction filtered.

Yield: 0.76 g (87% of theory),

Melting point: 290°–300° C. (decomp.)

| | C | H | N | Cl |
|---|---|---|---|---|
| Calc.: | 57.85 | 6.01 | 9.64 | 8.13 |
| Found: | 57.58 | 6.27 | 9.52 | 8.05 |

$R_f$ value: 0.67 (silica gel; methylene chloride/methanol=8:2) Mass spectrum: $M^+$=399

The following compounds are obtained analogously to Example 2:

(1) 2-[4-[4-(carboxymethyl)-piperidinocarbonyl]-phenyl]-4,5,6,7-tetrahydro-thiazolo[5,4-c]pyridine-hydrochloride The compound from Example 3(1) is used.

Melting point: 255°–258° C. (decomp.) $R_f$ value: 0.28 (silica gel; methylene chloride/methanol/conc. ammonia= 8:2:0.2) Mass spectrum: $M^+$=385

(2) 2-[4-[(trans-4-methoxycarbonyl-cyclohexyl)-aminocarbonyl]-phenyl]-4,5,7,8-tetrahydro-6H-thiazolo[4,5-d]azepine-hydrochloride The compound from Example 1(2) is used. The reaction is carried out in a 1:1 mixture of methylene chloride and ether saturated with hydrogen chloride.

Melting point: 312°–316° C. (decomp.) $R_f$ value: 0.33 (silica gel; methylene chloride/methanol/conc. ammonia= 9:1:0.1) Mass spectrum: $M^+$=413

(3) 2-[3-[(trans-4-methoxycarbonyl-cyclohexyl)-aminocarbonyl]-phenyl]-4,5,7,8-tetrahydro-6H-thiazolo[4,5-d]azepine-hydrochloride The compound from Example 1(3) is used. The reaction is carried out in a 1:1:0.5 mixture of methylene chloride, methanol and ether saturated with hydrogen chloride.

Melting point: 108°–110° C. (decomp.) $R_f$ value: 0.14 (silica gel; methylene chloride/methanol=9:1) Mass spectrum: $M^+$=413

(4) 2-[4-[(trans-4-methoxycarbonyl-cyclohexyl)-aminocarbonyl]-2-methyl-phenyl]-4,5,6,7-tetrahydro-thiazolo[5,4-c]pyridine-dihydrochloride The compound from Example 1(7) is used. The reaction is carried out in a 1:1:2 mixture of methylene chloride, methanol and ether saturated with hydrogen chloride.

Melting point: from 250° C. (decomp.) $R_f$ value: 0.40 (silica gel; methylene chloride/methanol/conc. ammonia= 9:1:0.1) Mass spectrum: $M^+$=413

Example 3

5-tert.Butyloxycarbonyl-2-[4-[(trans-4-carboxy-cyclohexyl)-aminocarbonyl]-phenyl]-4,5,6,7-tetrahydro-thiazolo[5,4-c]pyridine A solution of 0.60 g of 5-tert.butyloxycarbonyl-2-[4-[(trans-4-methoxycarbonyl)-aminocarbonyl]-phenyl]-4,5,6,7-tetrahydro-thiazolo[5,4-c]pyridine and 2.2 ml of a 1.4N aqueous lithium hydroxide solution in 10 ml of tetrahydrofuran and 10 ml of methanol is stirred at ambient temperature for 2 days. Then it is neutralised with 3 ml of 1N hydrochloric acid and the solvent is partially eliminated under reduced pressure. The precipitate is suction filtered and washed with water. The solid matter is dissolved in tetrahydrofuran, the solution is dried over magnesium sulphate and the solvent is evaporated down.

Yield: 0.40 g (69 % of theory), $R_f$ value: 0.30 (silica gel: methylene chloride/methanol=9:1) Mass spectrum: $(M-H)^-$=484

The following compounds are obtained analogously to Example 3:

(1) 5-tert.butyloxycarbonyl-2-[4-[4-(carboxymethyl)piperidinocarbonyl]-phenyl]-4,5,6,7-tetrahydro-thiazolo[5,4-c]pyridine $R_f$ value: 0.31 (silica gel: methylene chloride/methanol=9:1) Mass spectrum: $(M-H)^-$=484

(2) 6-tert.butyloxycarbonyl-2-[4-[(trans-4-carboxy-cyclohexyl)-aminocarbonyl]-phenyl]-4,5,7,8-tetrahydro-thiazolo[4,5-d]azepine $R_f$ value: 0.27 (silica gel: methylene chloride/methanol=9:1) Mass spectrum: $M^+$=499

(3) 2-[4-[(trans-4-carboxy-cyclohexyl)-aminocarbonyl]-phenyl]-6-methyl-4,5,7,8-tetrahydro-thiazolo[4,5-d]azepine Melting point: >320° C. (decomp.) $R_f$ value: 0.62 (silica gel: methylene chloride/methanol/conc. ammonia=7:3:0.5) Mass spectrum: $M^+$=413

(4) 2-[3-[(trans-4-carboxy-cyclohexyl)-aminocarbonyl]-phenyl]-4,5,7,8-tetrahydro-6H-thiazolo[4,5-d]azepine $R_f$ value: 0.27 (silica gel; methylene chloride/methanol/conc. ammonia=7:3:0.5) Mass spectrum: $M^+$=399

(5) 2-[1-[(trans-4-carboxy-cyclohexyl)-aminocarbonyl]-piperid-4-yl]-4,5,6,7-tetrahydro-thiazolo[5,4-c]pyridine Melting point: 216°–220° C. (decomp.) $R_f$ value: 0.36 (silica gel: methylene chloride/methanol/conc. ammonia=7:3:0.3) Mass spectrum: $M^+$=392

(6) 2-[1-[(trans-4-carboxy-cyclohexyl)-aminocarbonyl]-piperid-4-yl]-4,5,7,8-tetrahydro-6H-thiazolo[4,5-d]azepine The solvent is evaporated off under reduced pressure and the residue is chromatographed over silica gel.

Melting point: 248°–252° C. (decomp.) $R_f$ value: 0.22 (silica gel: methylene chloride/methanol/conc. ammonia=7:3:0.5) Mass spectrum: $M^+$=406

(7) 2-[4-[4-(carboxymethyl)-piperidinocarbonyl]-phenyl]-1H-imidazo[4,5-c]pyridine $R_f$ value: 0.62 (silica gel: methylene chloride/methanol/acetic acid=8:2:0.2) Mass spectrum: $M^+$=364

(8) 2-[4-[(trans-4-carboxy-cyclohexyl)-aminocarbonyl]-phenyl]-1H-imidazo[4,5-c]pyridine $R_f$ value: 0.25 (silica gel; methylene chloride/methanol/acetic acid=8:2:0.2) Mass spectrum: $M^+$=364

(9) 2-[4-[(trans-4-carboxy-cyclohexyl)-aminocarbonyl]-phenyl]-5-methyl-4,5,6,7-tetrahydro-imidazo[4,5-c]pyridine After neutralisation with 1N hydrochloric acid the solvent is evaporated off under reduced pressure and the residue is chromatographed. $R_f$ value: 0.33 (silica gel: methylene chloride/methanol/conc. ammonia=6:4:0.4) Mass spectrum: $M^+$=382

(10) 2-[4-[(trans-4-carboxy-cyclohexyl)-aminocarbonyl]-phenyl]-5-methyl-imidazo[5,4-c]pyridine $R_f$ value: 0.06 (silica gel: methylene chloride/methanol/acetic acid =8:2:0.2) Mass spectrum: $M^+$=378

(11) 2-[4-[(trans-4-carboxy-cyclohexyl)-aminocarbonyl]-2-methyl-phenyl]-4,5,7,8-tetrahydro-6H-thiazolo[4,5-d]azepine

(12) 2-[1-[(trans-4-carboxy-cyclohexyl)-aminocarbonyl]-piperid-4-yl]-6-methyl-4,5,7,8-tetrahydro-thiazolo[4,5-d]azepine $R_f$ value: 0.44 (silica gel; methylene chloride/methanol/conc. ammonia=7:3:0.5) Mass spectrum: $M^+$=420

(13) 2-[1-[N-(trans-4-carboxy-cyclohexyl)-N-methyl-aminocarbonyl]-piperid-4-yl]-4,5,7,8-tetrahydro-6H-thiazolo[4,5-d]azepine

(14) 2-[4-[(trans-4-carboxy-cyclohexyl)-methyloxy]-phenyl]-4,5,6,7-tetrahydro-thiazolo[5,4-c]pyridine

(15) 2-[trans-4-[(trans-4-carboxy-cyclohexyl)-carbonylamino]cyclohexyl]-4,5,7,8-tetrahydro-6H-thiazolo[4,5-d]azepine

(16) 2-[trans-4-[(trans-4-carboxy-cyclohexyl)-carbonylamino]-cyclohexyl]-4,5,6,7-tetrahydro-thiazolo[5,4-c]pyridine

(17) 2-[4-[N-benzyl-N-(trans-4-carboxy-cyclohexyl)-aminocarbonyl]-piperidyl]-4,5,6,7-tetrahydro-thiazolo[5,4-c]pyridine

(18) 2-[4-[(trans-4-carboxy-cyclohexyl)-carbonylamino]-phenyl]-4,5,7,8-tetrahydro-6H-thiazolo[4,5-d]azepine

(19) 2-[4-[(trans-4-carboxy-cyclohexyl)-oxymethyl]-phenyl]-4,5,6,7-tetrahydro-thiazolo[5,4-c]pyridine

(20) 2-[2-[(trans-4-carboxy-cyclohexyl)-aminocarbonyl]-pyrid-4-yl]-4,5,7,8-tetrahydro-6H-thiazolo[4,5-d]azepine

(21) 2-[4-[4-(2-carboxy-ethyl)-piperidinocarbonyl]-phenyl]-4,5,6,7-tetrahydro-thiazolo[5,4-c]pyridine

(22) 2-[trans-4-[(trans-4-carboxy-cyclohexyl)-aminocarbonyl]-cyclohexyl]-1-methyl-imidazo[4,5-c]pyridine

(23) 2-[1-[(trans-4-carboxy-cyclohexyl)-aminocarbonyl]-piperid-4-yl]-1-methyl-imidazo[4,5-c]pyridine

(24) 2-[1-[(trans-4-carboxy-cyclohexyl)-aminocarbonyl]-piperid-4-yl]-1-methyl-4,5,6,7-tetrahydro-imidazo[4,5-c]pyridine

(25) 2-[trans-4-[(trans-4-carboxy-cyclohexyl)-aminocarbonyl]-cyclohexyl]-1-methyl-4,5,6,7-tetrahydro-imidazo[4,5-c]pyridine

(26) 2-[4-[(trans-4-carboxy-cyclohexyl)-carbonylamino]-phenyl]-4,5,7,8-tetrahydro-6H-1,3-oxazolo[4,5-d]azepine

(27) 2-[4-[(trans-4-carboxy-cyclohexyl)-aminocarbonyl]-2-fluoro-phenyl]-4,5,7,8-tetrahydro-6H-thiazolo[4,5-d]azepine

(28) 2-[4-[(trans-4-carboxy-cyclohexyl)-aminomethyl]-phenyl]-4,5,7,8-tetrahydro-6H-thiazolo[4,5-d]azepine

(29) 2-[4-[4-carboxy-piperidinocarbonyl)-methyl]-phenyl]-4,5,6,7-tetrahydro-thiazolo[5,4-c]pyridine

(30) 2-[4-[2-(4-carboxy-piperidino)-ethyl]-phenyl]-4,5,6,7-tetrahydro-thiazolo[5,4-c]pyridine

(31) 2-[trans-4-[(trans-4-carboxy-cyclohexyl)-aminocarbonyl]-cyclohexyl]-4,5,6,7-tetrahydro-thiazolo[5,4-c]pyridine

(32) 2-[3-bromo-4-[(trans-4-carboxy-cyclohexyl)-carbonylamino]-phenyl]-4,5,7,8-tetrahydro-6H-thiazolo[4,5-d]azepine

(33) 2-[1-[(trans-4-carboxy-cyclohexyl)-aminocarbonyl]-piperid-3-yl]-4,5,7,8-tetrahydro-6H-thiazolo[4,5-d]azepine

(34) 5-allyloxycarbonyl-2-[1-[(trans-4-carboxy-cyclohexyl)-aminocarbonyl]-piperid-4-yl]-4,5,6,7-tetrahydro-thiazolo[5,4-c]pyridine

(35) 6-allyloxycarbonyl-2-[1-[(trans-4-carboxy-cyclohexyl)-aminocarbonyl]-piperid-4-yl ]-4,5,7,8-tetrahydro-thiazolo[4,5-d]azepine

(36) 2-[4-[(trans-4-carboxy-cyclohexyl)-aminocarbonyl]-piperazinyl]-4,5,6,7-tetrahydro-thiazolo[5,4-c]pyridine

(37) 5-tert.butyloxycarbonyl-2-[4-[(trans-4-carboxy-cyclohexyl)-aminocarbonyl]-2-methyl-phenyl]-4,5,6,7-tetrahydro-thiazolo[5,4-c]pyridine Melting point: from 210° C. (sintering) $R_f$ value: 0.33 (silica gel: methylene chloride/methanol=9:1)

(38) 6-tert.butyloxycarbonyl-2-[trans-4-[(trans-4-carboxy-cyclohexyl)-aminocarbonyl]-cyclohexyl]-4,5,7,8-tetrahydro-thiazolo[4,5-d]azepine Melting point: from 260° C. (sintering) $R_f$ value: 0.44 (silica gel: methylene chloride/methanol=9:1) Mass spectrum: $M^+$=505

Example 4

2-[4-[(trans-4-Carboxy-cyclohexyl)-aminocarbonyl]-phenyl]-4,5,6,7-tetrahydro-thiazolo[5,4-c]-pyridine-trifluoroacetate A solution of 0.40 g of 5-tert.butyloxycarbonyl-2-[4-[(trans-4-carboxy-cyclohexyl)-aminocarbonyl]-phenyl]-4,5,6,7-tetrahydro-thiazolo[5,4-c]pyridine in 40 ml of methylene chloride and 5 ml of trifluoroacetic acid is stirred at ambient temperature for 2 hours. Then the solvent and the trifluoroacetic acid are removed under reduced pressure, the residue obtained is triturated with ether and suction filtered.

Yield: 0.50 g (quantitative),

Melting point: 306°–316° C. (decomp.) $R_f$ value: 0.12 (silica gel; methylene chloride/methanol=8:2) Mass spectrum: $M^+$=385

The following compounds are obtained analogously to Example 4:

(1) 2-[4-[(trans-4-carboxy-cyclohexyl)-aminocarbonyl]-phenyl]-4,5,7,8-tetrahydro-6H-thiazolo[4,5-d]azepine-trifluoroacetate Melting point: 300°–308° C. (decomp.) $R_f$ value: 0.11 (silica gel; methylene chloride/methanol=2:1)

| Calc.: | C 53.79 | H 5.10 | N 8.18 | S 6.24 |
|---|---|---|---|---|
| Found: | 53.55 | 5.23 | 8.14 | 6.14 |
| Mass spectrum: $(M + H)^+ = 400$ | | | | |

(2) 2-[1-[(trans-4-carboxy-cyclohexyl)-aminocarbonyl]-piperid-4-yl]-4,5,6,7-tetrahydro-thieno[4,5-c]pyridine-trifluoroacetate (3) 2-[4-[(trans-4-carboxy-cyclohexyl)-aminocarbonyl]-2-methyl-phenyl]-4,5,6,7-tetrahydro-thiazolo[5,4-c]pyridine-trifluoroacetate Melting point: 240°–241° C. (decomp.), $R_f$ value: 0.33 (silica gel; methylene chloride/methanol/conc. ammonia=7:3:0.5)

| Calc.: | C 53.79 | H 5.10 | N 8.18 | S 6.24 |
|---|---|---|---|---|
| Found: | 53.71 | 5.32 | 8.07 | 6.40 |
| Mass spectrum: $M^+ = 399$ | | | | |

(4) 2-[trans-4-[(trans-4-carboxy-cyclohexyl)-aminocarbonyl]-cyclohexyl]-4,5,7,8-tetrahydro-6H-thiazolo[4,5-d]azepine-trifluoroacetate Melting point: from 134° C. (sintering), $R_f$ value: 0.29 (silica gel; methylene chloride/methanol/conc. ammonia=7:3:0.5) Mass spectrum: $M^+$=405

Example 5

2-[4-[(trans-4-Methoxycarbonyl-cyclohexyl)-aminocarbonyl]phenyl]-6-methyl-4,5,7,8-tetrahydro-thiazolo[4,5-d]azepine A suspension of 300 mg of 2-[4-[(trans-4-methoxycarbonyl-cyclohexyl)-aminocarbonyl]-phenyl]-4,5,7,8-tetrahydro-6H-thiazolo[4,5-d]azepine, 80 mg of sodium carbonate and 70 mg of potassium acetate in 0.25 ml of formic acid and 0.12 ml of a 33% aqueous formaldehyde solution is heated over a steam bath for 2 hours. After the suspension has been evaporated down in vacuo, the residue obtained is dissolved in water and sodium hydrogen carbonate is added until an alkaline reaction mixture is obtained. After extraction of the aqueous phase with ethyl acetate, the organic phase is washed with water, dried and the solvent is eliminated under reduced pressure.

Yield: 80 mg (30% of theory), $R_f$ value: 0.53 (silica gel; methylene chloride/methanol/conc. ammonia=9:1:0.1) Mass spectrum: $M^+$=427

Example 6

2-[1-[(trans-4-Methoxycarbonyl-cyclohexyl)-aminocarbonyl]-piperid-4-yl]-6-trifluoroacetyl-4,5,7,8-tetrahydro-thiazolo[4,5-d]azepine A solution of 1.68 ml of triethylamine in 10 ml of tetrahydrofuran is added dropwise at −15° C, within 30 minutes, to a solution of 1.0 g of 4-nitro-phenyl-chloroformate and 0.95 g of methyl trans-4-amino-cyclohexanecarboxylate-hydrochloride in 50 ml of tetrahydrofuran. The mixture is stirred for 1 hour at −15° C. and then a solution of 19 g of 6-trifluoroacetyl-2-(piperid-4-yl)-4,5,7,8-tetrahydro-thiazolo[4,5-d]azepine-hydrobromide and 1.4 ml of triethylamine in 20 ml of tetrahydrofuran is added dropwise thereto. The mixture is allowed to come up to ambient temperature and stirred for 16 hours. Then the solvent is eliminated under reduced pressure and the residue obtained is distributed between water and ethyl acetate. The organic phase is washed with water, 0.1N ammonia solution and water and dried over magnesium sulphate. The solvent is evaporated off under reduced pressure and the residue is chromatographed over silica gel.

Yield: 1.2 g (58% of theory),

Melting point: 167°–169° C. $R_f$ value: 0.44 (silica gel; methylene chloride/methanol=9:1) Mass spectrum: $M^+$=516

The following compounds are obtained analogously to Example 6:

(1) 2-[1-[(trans-4-methoxycarbonyl-cyclohexyl)-aminocarbonyl]-piperid-4-yl]-5-trifluoroacetyl-4,5,6,7-tetrahydro-thiazolo[5,4-c]pyridine $R_f$ value: 0.24 (silica gel; methylene chloride/methanol=19:1) Mass spectrum: $M^+$=502

(2) 2-[1-[(trans-4-methoxycarbonyl-cyclohexyl)-aminocarbonyl]-piperid-4-yl]-6-methyl-4,5,7,8-tetrahydro-thiazolo[4,5-d]azepine $R_f$ value: 0.31 (silica gel; methylene chloride/methanol=9:1; 2×) Mass spectrum: $M^+$=434

(3) 6-allyloxycarbonyl-2-[1-[(trans-4-methoxycarbonyl-cyclohexyl)-aminocarbonyl]-piperid-4-yl]-4,5,7,8-tetrahydro-thiazolo[4,5-d]azepine (4) 5-allyloxycarbonyl-2-[1-[(trans-4-methoxycarbonyl-cyclohexyl)-aminocarbonyl]-piperid-4-yl]-4,5,6,7-tetrahydro-thiazolo[5,4-c]pyridine

Example 7

2-[1-[(trans-4-Isobutyloxycarbonyl-cyclohexyl)-aminocarbonyl]-piperid-4-yl]-4,5,7,8-tetrahydro-6H-thiazolo[4,5-d]azepine-hydrochloride Hydrogen chloride is piped through a solution of 200 mg of 2-[1-[(trans-4-carboxy-cyclohexyl)-aminocarbonyl]-piperid-4-yl]-4,5,7,8-tetrahydro-6H-thiazolo[4,5-d]azepine in 20 ml of isobutanol and 5 ml of methylene chloride until saturation point is reached. After 2 days' stirring at ambient temperature, ether is added and the precipitate is suction filtered.

Yield: 240 mg (91% of theory),

Melting point: 214°–216° C. (decomp.) $R_f$ value: 0.22 (silica gel; methylene chloride/methanol=8:2) Mass spectrum: $M^+$=462

The following compounds are obtained analogously to Example 7:

(1) 2-[1-[(trans-4-methoxycarbonyl-cyclohexyl)-aminocarbonyl]-piperid-4-yl]-4,5,7,8-tetrahydro-6H-thiazolo[4,5-d]azepine-hydrochloride The reaction is carried out in methanol/ether (4:1).

Melting point: 205°–208° C. (decomp.) $R_f$ value: 0.25 (silica gel; methylene chloride/methanol=8:2) Mass spectrum: $M^+$=420

(2) 2-[1-[(trans-4-ethoxycarbonyl-cyclohexyl)-aminocarbonyl]-piperid-4-yl]-4,5,7,8-tetrahydro-6H-thiazolo[4,5-d]azepine-hydrochloride The reaction is carried out in ethanol.

Melting point: 200°–210° C. (decomp.) $R_f$ value: 0.25 (silica gel; methylene chloride/methanol=8:2) Mass spectrum: $M^+$=434

(3) 2-[1-[(trans-4-isopropoxycarbonyl-cyclohexyl)-aminocarbonyl]-piperid-4-yl]-4,5,7,8-tetrahydro-6H-thiazolo[4,5-d]azepine-hydrochloride The reaction is carried out in isopropanol.

Melting point: 200°–210° C. (decomp.) $R_f$ value: 0.21 (silica gel; methylene chloride/methanol=8:2) Mass spectrum: $M^+$=448

(4) 2-[1-[(trans-4-ethoxycarbonyl-cyclohexyl)-aminocarbonyl]-piperid-4-yl]-4,5,6,7-tetrahydro-thiazolo[5,4-c]pyridine-hydrochloride The reaction is carried out in ethanol.

Melting point: 210°–241° C. (decomp.) $R_f$ value: 0.36 (silica gel; methylene chloride/methanol/conc. ammonia= 9:1:0.1) Mass spectrum: $M^+$=420

(5) 2-[1-[(trans-4-isobutyloxycarbonyl-cyclohexyl)-aminocarbonyl]-piperid-4-yl]-4,5,6,7-tetrahydro-thiazolo[5,4-c]pyridine-hydrochloride The reaction is carried out in isobutanol.

Melting point: 220°–238° C. (decomp.) $R_f$ value: 0.36 (silica gel; methylene chloride/methanol/conc. ammonia= 9:1:0.1) Mass spectrum: $M^+$=448

Example 8

2-[4-[(trans-4-Methoxycarbonyl-cyclohexyl)-aminocarbonyl]-phenyl]-5-methyl-4,5,6,7-tetrahydro-1H-imidazo[4,5-c]pyridine A solution of 740 mg of 2-[4-[(trans-4-methoxycarbonyl-cyclohexyl)-aminocarbonyl]-phenyl]-5-methyl-5H-imidazo[5,4-c]pyridine in 50 ml of acetic acid is hydrogenated for 17 hours at ambient temperature in the presence of 0.4 g platinum dioxide under a hydrogen pressure of 5 bar. Then the catalyst is suction filtered off and the solution is evaporated down under reduced pressure. The residue is triturated with ethyl acetate and the precipitate is suction filtered.

Yield: 650 mg (87% of theory), $R_f$ value: 0.16 (silica gel; methylene chloride/methanol=8:2) Mass spectrum: $M^+$=396

Example 9

5-Allyloxycarbonyl-2-[1-[[trans-4-[(pivaloyloxymethyl)-oxycarbonyl]-cyclohexyl]-aminocarbonyl]-piperid-4-yl]-4,5,6,7-tetrahydrothiazolo[5,4-c]pyridine Prepared by stirring a suspension of 5-allyloxycarbonyl-2-[1-[(trans-4-carboxy-cyclohexyl)-aminocarbonyl]-piperid-4-yl]-4,5,6,7-tetrahydro-thiazolo[5,4-c]-pyridine, 2 equivalents of chloromethyl pivalate, 2 equivalents of potassium iodide, 2 equivalents of potassium hydrogen carbonate and 2 equivalents of potassium carbonate in dimethylformamide at ambient temperature for 3 days.

The following compound is obtained analogously to Example 9:

(1) 6-allyloxycarbonyl-2-[1-[[trans-4-[[1-(ethoxycarbonyloxy)-ethyl]-oxycarbonyl]-cyclohexyl]aminocarbonyl]-piperid-4-yl]-4,5,7,8-tetrahydro-thiazolo[4,5-d] azepine The reaction is carried out with 1-(ethoxycarbonyloxy)ethylchloride in dimethylsulphoxide.

Example 10

2-[1-[[trans-4-[[1-(Ethoxycarbonyloxy)-ethyl]-oxycarbonyl]-cyclohexyl]-aminocarbonyl]piperid-4-yl]-4,5,7,8-tetrahydro-6H-thiazolo[4,5-d]azepine Prepared by dropwise addition of one equivalent of morpholine to 6-allyloxycarbonyl-2-[1-[[trans-4-[[1-(ethoxycarbonyloxy)-ethyl]-oxycarbonyl]-cyclohexyl-thiazolo[4,5-d]azepine and 0.1 equivalent of tetrakis-(triphenylphosphine)-palladium(O) in tetrahydrofuran followed by one hours' stirring at ambient temperature. The following compound is obtained analogously to Example 10:

(1) 2-[1-[[trans-4-[(pivaloyloxymethyl)-oxycarbonyl]-cyclohexyl]-aminocarbonyl]-piperid-4-yl]-4,5,6,7-tetrahydro-thiazolo[5,4-c]pyridine

Example 11

Dry ampoule containing 2.5 mg of active substance per 1 ml

| Composition: | |
| --- | --- |
| Active substance | 2.5 mg |
| Mannitol | 50.0 mg |
| Water for injections ad | 1.0 ml |

Preparation:

The active substance and mannitol are dissolved in water. After transferring the solution to the ampoule, it is freeze-dried.

At the point of use, the solution is made up with water for injections.

Example 12

Dry ampoule containing 35 mg of active substance per 2 ml

| Composition: | |
| --- | --- |
| Active substance | 35.0 mg |
| Mannitol | 100.0 mg |
| Water for injections ad | 2.0 ml |
| Preparation: | |

The active substance and mannitol are dissolved in water. After transferring the solution to the ampoule, it is freeze-dried.

At the point of use, the solution is made up with water for injections.

Example 13

Tablet containing 50 mg of active substance

| Composition: | |
| --- | --- |
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granules. From this mixture, tablets are compressed, biplanar, facetted on both sides and notched on one side. Diameter of tablets: 9 mm.

Example 14

Tablet containing 350 mg of active substance

| Composition: | |
| --- | --- |
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granules. From this mixture, tablets are compressed, biplanar, facetted on both sides and notched on one side. Diameter of tablets: 12 mm.

Example 15

Capsules containing 50 mg of active substance

| Composition: | |
| --- | --- |
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation:

(1) is triturated with (3). This triturate is added to the mixture of (2) and (4), with thorough mixing.

This powdered mixture is packed into size 3 hard gelatin oblong capsules in a capsule filling machine.

Example 16

Capsules containing 350 mg of active substance

| Composition: | |
|---|---|
| (1) Active substance | 350.0 mg |
| (2) Dried corn starch | 46.0 mg |
| (3) Powdered lactose | 30.0 mg |
| (4) Magnesium stearate | 4.0 mg |
| | 430.0 mg |

Preparation:

(1) is triturated with (3). This triturate is added to the mixture of (2) and (4), with thorough mixing. This powdered mixture is packed into size 0 hard gelatin oblong capsules in a capsule filling machine.

What is claimed is:

1. A bicyclic heterocyclic compound of the formula I

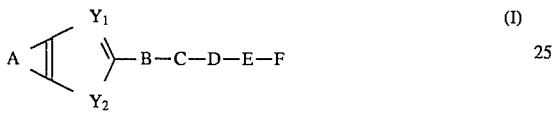

wherein $Y_1$ denotes a nitrogen atom;

$Y_2$ denotes a nitrogen atom substituted by a group $R_1$, wherein $R_1$ is a hydrogen atom or a $C_{1-3}$alkyl group, or $Y_2$ denotes a sulphur atom;

A denotes a —CH=CH—N=CH—, —CH=N—CH=CH—, —(CH$_2$)$_2$—NR$_2$—CH$_2$— or —(CH$_2$)$_2$—NR$_2$—(CH$_2$)$_2$— bridge, wherein R$_2$ denotes a hydrogen atom, a $C_{1-3}$-alkyl, allyloxycarbonyl or trifluoromethylcarbonyl group or an alkoxycarbonyl group having a total of 2 to 5 carbon atoms;

B denotes a phenylene group optionally substituted by a fluorine, chlorine or bromine atom or by a methyl or ethyl group, wherein additionally a methine group may be substituted by a nitrogen atom, or B denotes a 1,4-cyclohexylene, 1-3-piperidinylene, 1,4-piperidinylene or 1,4-piperazinylene group;

C denotes a —CH$_2$—, —CH$_2$CH$_2$— or —CO— group, a —CH$_2$—CO— or —NR$_4$—CO— group, wherein the carbonyl group in each case is bound to group D and R$_4$ denotes a hydrogen atom or a $C_{1-3}$-alkyl group, or C denotes a —CH$_2$—NR$_4$—, —NR$_4$—CH$_2$—, —O—CH$_2$— or —CH$_2$—O— group, wherein the nitrogen or oxygen atom cannot be bound directly or via a single carbon atom to a nitrogen atom of groups B or D and R$_4$ is as hereinbefore defined;

D denotes a 1,4-cyclohexylene group or a 1,4-piperidinylene group which is bound via the nitrogen atom in the 1-position to the group C, or D denotes an —NR$_5$-1,4-cyclohexylene group, wherein R$_5$ denotes a hydrogen atom or a methyl, ethyl or benzyl group;

E denotes a $C_{1-3}$-alkylene group or a bond; and

F denotes a carbonyl group substituted by an R$_8$O— group, or F denotes an R$_9$CO—O—CHR$_6$—O—CO— group wherein R$_6$ denotes a hydrogen atom or a methyl group, R$_8$ denotes a hydrogen atom or a $C_{1-5}$-alkyl group and R$_9$ denotes a $C_{1-5}$-alkyl group or a methoxy or ethoxy group;

or a tautomer or pharmaceutically acceptable salt thereof.

2. A compound of the formula I

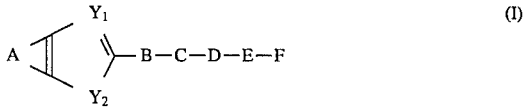

wherein $Y_1$ denotes a nitrogen atom;

$Y_2$ denotes an —NH group or a sulphur atom;

A denotes a —(CH$_2$)$_2$—NR$_2$—CH$_2$—or —(CH$_2$)$_2$—NR$_2$—(CH$_2$)$_2$— bridge wherein R$_2$ denotes a hydrogen atom, a methyl, ethyl or trifluoromethylcarbonyl group or an alkoxycarbonyl group having a total of 2 to 5 carbon atoms;

B denotes an optionally methyl-substituted phenylene group or a 1,4-cyclohexylene, 1,4-piperidinylene or 1,4-piperazinylene group;

C denotes a —CO group;

D denotes a 1,4-cyclohexylene group or a 1,4-piperidinylene group which is bound via the nitrogen atom in the 1-position to the group C, or denotes an —NR$_5$-1,4-cyclohexylene group, wherein R$_5$ denotes a hydrogen atom or a methyl group;

E denotes a methylene group or a bond; and

F denotes a carbonyl group substituted by an R$_8$O— group, wherein

R$_8$ denotes a hydrogen atom or a $C_{1-5}$-alkyl group;

or a tautomer or pharmaceutically acceptable salt thereof.

3. A compound selected from the group consisting of:

(a) 2-[4-[(trans-4-carboxy-cyclohexyl)-aminocarbonyl]-phenyl]-4,5,6,7-tetrahydro-thiazolo[5,4-c]pyridine, (b) 2-[4-[(trans-4-methoxycarbonyl-cyclohexyl)-aminocarbonyl]-phenyl]-4,5,6,7-tetrahydro-thiazolo[5,4-c]pyridine, (c) 2-[4-[(trans-4-carboxy-cyclohexyl)-aminocarbonyl]-phenyl]-4,5,7,8-tetrahydro-6H-thiazolo[4,5-d]azepine, (d) 2-[4-[(trans-4-methoxycarbonyl-cyclohexyl)-aminocarbonyl]-phenyl]-4,5,7,8-tetrahydro-6H-thiazolo[4,5-d]azepine, (e) 2-[1-[(trans-4-carboxy-cyclohexyl)-aminocarbonyl]-piperid-4-yl]-4,5,6,7-tetrahydro-thiazolo[5,4-c]pyridine, (f) 2-[1-[(trans-4-carboxy-cyclohexyl)-aminocarbonyl]-piperid-4-yl]-4,5,7,8-tetrahydro-6H-thiazolo[4,5-d]azepine, (g) 2-[1-[(trans-4-methoxycarbonyl-cyclohexyl)-aminocarbonyl]-piperid-4-yl]-4,5,7,8-tetrahydro-6H-thiazolo[4,5-d]azepine, (h) 2-[1-[(trans-4-isobutyloxycarbonyl-cyclohexyl)-aminocarbonyl]-piperid-4-yl]-4,5,7,8-tetrahydro-6H-thiazolo[4,5-d]azepine, (i) 2-[4-[(trans-4-carboxy-cyclohexyl)-aminocarbonyl]-2-methyl-phenyl]-4,5,6,7-tetrahydro-thiazolo[5,4-c]pyridine, (j) 2-[4-[(trans-4-methoxycarbonyl-cyclohexyl)-aminocarbonyl]-2-methyl-phenyl]-4,5,6,7-tetrahydro-thiazolo[5,4-c]pyridine, (k) 2-[trans-4-[(trans-4-carboxy-cyclohexyl)-aminocarbonyl]-cyclohexyl]-4,5,7,8-tetrahydro-6H-thiazolo[4,5-d]azepine, (l) 2-[1-[(trans-4-ethoxycarbonyl-cyclohexyl)-aminocarbonyl]-piperid-4-yl]-4,5,7,8-tetrahydro-6H-thiazolo[4,5-d]azepine, (m) 2-[1-[(trans-4-isopropoxycarbonyl-cyclohexyl)-aminocarbonyl]-piperid-4-yl]-4,5,7,8-tetrahydro-6H-thiazolo[4,5-d]azepine and the tautomers and pharmaceutically acceptable salts thereof.

4. A compound in accordance with claim 1, wherein A is a —$(CH_2)_2$—$NR_2$—$CH_2$— or —$(CH_2)_2$—$NR_2$—$(CH_2)_2$— bridge.

5. A compound in accordance with claim 4, wherein $Y_2$ is a sulfur atom.

6. A pharmaceutical composition comprising a compound according to claim 1, 4, 5, 2, or 3, optionally together with one or more inert carriers and/or diluents.

7. A method for treating venous or arterial thrombosis, which comprises administering to a host suffering from the same a therapeutic amount of a compound in accordance with claims 1, 4, 5, 2, or 3.

* * * * *